(12) United States Patent
Kimock et al.

(10) Patent No.: US 11,806,214 B2
(45) Date of Patent: Nov. 7, 2023

(54) MEDICAL HEADGEAR

(71) Applicant: Neatcap, LLC, Bethlehem, PA (US)

(72) Inventors: Fred M. Kimock, Macungie, PA (US); Zachary Rambo, Melrose, MA (US); Edward G. Thear, Kure Beach, NC (US)

(73) Assignee: Neatcap, LLC, Bethlehem, PA (US)

( * ) Notice: Subject to any disclaimer, the term of this patent is extended or adjusted under 35 U.S.C. 154(b) by 574 days.

(21) Appl. No.: 16/887,847

(22) Filed: May 29, 2020

(65) Prior Publication Data

US 2020/0289325 A1   Sep. 17, 2020

Related U.S. Application Data

(63) Continuation-in-part of application No. 15/881,111, filed on Jan. 26, 2018, now Pat. No. 11,185,447, which is a continuation-in-part of application No. 14/626,325, filed on Feb. 19, 2015, now Pat. No. 10,413,696.

(51) Int. Cl.
*A61F 11/14*     (2006.01)
*A61M 16/06*   (2006.01)
*A61F 9/04*       (2006.01)

(52) U.S. Cl.
CPC ......... *A61F 11/14* (2013.01); *A61M 16/0683* (2013.01); *A61F 9/045* (2013.01); *A61M 16/0666* (2013.01); *A61M 2205/0216* (2013.01); *A61M 2240/00* (2013.01)

(58) Field of Classification Search
CPC   A61F 11/06; A61F 11/14; A61F 11/08; A61F 11/085; A61F 11/12; A61F 11/00; A61M 2205/0216
See application file for complete search history.

(56) References Cited

U.S. PATENT DOCUMENTS

| 1,489,145 | A |   | 4/1924  | O'Keefe |
|---|---|---|---|---|
| 3,875,592 | A |   | 4/1975  | Aileo |
| 3,938,614 | A | * | 2/1976  | Ahs .......................... A61F 11/14 |
|   |   |   |   | 381/372 |
| 4,037,273 | A |   | 7/1977  | Labaire |
| 4,802,245 | A |   | 2/1989  | Miano |
| 4,805,239 | A |   | 2/1989  | Ciago |
| 4,830,138 | A |   | 5/1989  | Palmaer et al. |
| 4,905,322 | A | * | 3/1990  | Aileo ..................... A42B 3/166 |
|   |   |   |   | 181/129 |
| 4,907,576 | A |   | 3/1990  | Curlee |
| 5,038,412 | A |   | 8/1991  | Cionni |
| 5,058,606 | A |   | 10/1991 | Malkoff |
| 5,188,101 | A |   | 2/1993  | Tumolo |
| 5,243,709 | A |   | 9/1993  | Sheehan et al. |
| 5,420,381 | A |   | 5/1995  | Gardner, Jr. et al. |
| 5,713,078 | A |   | 2/1998  | DeAngelis |
| 5,887,286 | A |   | 3/1999  | Waldron |

(Continued)

FOREIGN PATENT DOCUMENTS

BR      PI0403859-2 B1    11/2010

*Primary Examiner* — Keri J Nelson
(74) *Attorney, Agent, or Firm* — Barley Snyder

(57) ABSTRACT

An earcup for a medical headgear includes a body and a gasket attached to the body and formed of an open-cell foam. The earcup with the body and the gasket is a frequency-dependent auditory filter providing sound attenuation generally increasing as a function of frequency.

15 Claims, 27 Drawing Sheets

(56) References Cited

U.S. PATENT DOCUMENTS

| | | | |
|---|---|---|---|
| 6,126,683 | A | 10/2000 | Momtaheni |
| 6,269,488 | B1 | 8/2001 | Jurgensen et al. |
| 7,841,446 | B2 * | 11/2010 | Leong .................... A61F 11/08 381/328 |
| 7,878,968 | B2 | 2/2011 | Wittmann-Price et al. |
| 8,526,658 | B1 | 9/2013 | Houston |
| 8,534,290 | B2 | 9/2013 | Karrman |
| 2004/0221370 | A1 | 11/2004 | Hannula et al. |
| 2007/0044206 | A1 | 3/2007 | Sato et al. |
| 2007/0235034 | A1 | 10/2007 | Weaver |
| 2008/0264715 | A1 | 10/2008 | Leong et al. |
| 2009/0178177 | A1 | 7/2009 | Fairclough et al. |
| 2009/0205900 | A1 | 8/2009 | Purcell et al. |
| 2009/0260134 | A1 | 10/2009 | Wittmann-Price et al. |
| 2012/0012418 | A1 | 1/2012 | Nilsson et al. |
| 2013/0133671 | A1 | 5/2013 | Fairclough et al. |
| 2014/0003614 | A1 | 1/2014 | Levitov et al. |

* cited by examiner

MEDICAL HEADGEAR

CROSS-REFERENCE TO RELATED APPLICATION

This application is a continuation-in-part of U.S. patent application Ser. No. 15/881,111, filed on Jan. 26, 2018, which is a continuation-in-part of U.S. patent application Ser. No. 14/626,325, filed on Feb. 19, 2015.

FIELD OF THE INVENTION

The invention generally relates to headgear, and more specifically to a medical headgear.

BACKGROUND

Approximately twelve percent of newborns are born preterm in the U.S. These preterm newborns frequently require long, expensive, and stressful hospital stays in neonatal intensive care units (NICUs), and present a number of unique challenges. Studies have shown that the total brain weight achieved at 34 weeks can be as little as 65% of that of a full term newborn, with the remaining brain development occurring outside the protection of the utero environment. Further studies have shown that preterm newborns exhibit decreased cerebral cortex volume and cerebellar growth when compared to their full term counterparts, frequently emerging from NICUs having developmental and neurosensory deficits.

Advances in preterm newborn developmental research suggest that the loud, atypical acoustic environments characteristic of NICUs may contribute to the decreased cerebral cortex volume and cerebellar growth, resulting in negative outcomes involving hearing, growth, and ultimately, cognition. Exposure of preterm newborns to environmental stimuli that do not correspond to the normal in-utero acoustic environment induces stress, which negatively impacts sleep, growth, and sensory development processes. The negative impact is thought to disrupt and alter normal brain development in response to the external environmental stimuli.

Generally, a mother's body and amniotic fluid surround a developing fetus, providing a natural acoustic filter, with sound attenuation increasing as a function of frequency. The gravid uterus plus amniotic fluid provides negligible sound attenuation of frequencies less than about 300 Hz, then sound attenuation increases monotonically up to 15-20 decibels (dB) at about 2,000 Hz. Above 2,000 Hz, the gravid uterus effectively blocks sound, i.e. attenuation is 15-20 dB or greater.

Attempts have been made to adapt NICUs to reduce the environmental noise levels, including the installation of low-noise incubation equipment and sound-absorbing materials in floors, walls, and ceilings. Other attempts include the use of single-bed NICU rooms to allow better control of the environmental noise levels. While these approaches do reduce some environmental noise, they are only marginally effective, and are often cost prohibitive for many institutions.

Further attempts to reduce environmental noise include the use of foam earcups that are placed over the ears of a preterm newborn, and attached through the use of an adhesive. While the foam earcups do provide limited sound attenuation, the filtered sound profile does not correspond to the normal in-utero acoustic environment. As a result, the effectiveness of the foam earcups is extremely limited.

Another unique challenge with preterm newborns is that their skin and facial features are very delicate and extremely susceptible to damage, such as tearing or pressure necrosis. This presents several problems for implementation of devices to support development.

Firstly, the foam earcups rely on a hydrogel adhesive to bond the earcup to the skin to form an acoustic seal. The hydrogel adhesive is very sensitive to conditions of application. If the foam ear cup is very lightly positioned, in order to prevent damage to the skin, the adhesive bond is very weak, and the bond between the earcups and the skin of the preterm newborn fails within a few hours. In other instances, the adhesive bond to the skin is too strong, and extreme care must be taken when peeling the bonded earcup away from the skin to remove the foam earcup. Often, the removal process results in damage to the skin, such as tearing or irritation.

Secondly, the underdeveloped lungs in preterm newborns frequently require respiratory support in the form of conventional mechanical ventilation, high frequency ventilation, or continuous positive airway pressure (CPAP) delivered through respiratory support tubes positioned in the oral cavity or nose by a nasal cannula. While there are many conventional respiratory support tube attachment devices available for full-term newborns and adults, these devices are not suited for the delicate skin or nasal septum of preterm newborns. Consequently, the respiratory support tubes are commonly attached to fabric caps by safety pins and rubber bands, or directly to the skin of the preterm newborn by medical tape. Extreme care must be taken during removal of the medical tape, to avoid injury to the preterm newborn.

Consequently, there is a strong need for a medical headgear that is suitable for use on preterm newborns, which reduces environmental noise to in-utero acoustic levels, and provides a stable support for attaching respiratory support tubes and other medical devices.

SUMMARY

An earcup for a medical headgear includes a body and a gasket attached to the body and formed of an open-cell foam. The earcup with the body and the gasket is a frequency-dependent auditory filter providing sound attenuation generally increasing as a function of frequency.

BRIEF DESCRIPTION OF THE DRAWINGS

The invention will now be described by way of example with reference to the accompanying figures, of which.

DETAILED DESCRIPTION OF THE EMBODIMENT(S)

Figure 1:
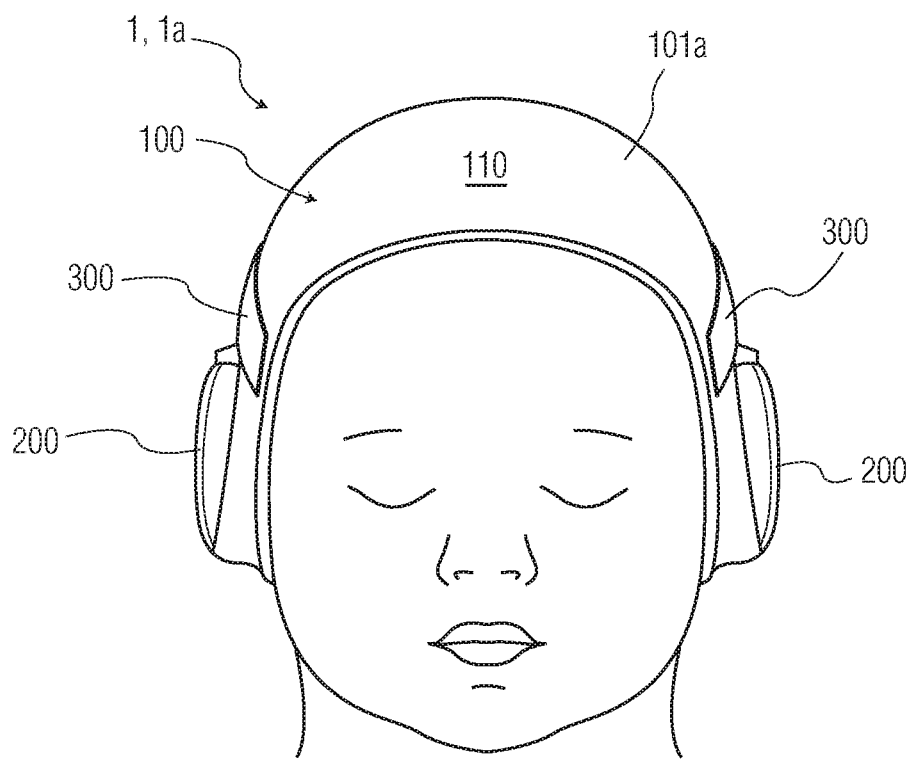
FIG. 1 is a front perspective view of a rear-closing medical headgear installed on a head of a preterm newborn.

In the embodiments of FIGS. 1-17, a medical headgear 1 has a flexible band 100, a pair of earcups 200, and a plurality of medical device fasteners 300.

The flexible band 100 is elongated, extending along a longitudinal axis, having an outer surface 101a and an inner surface 101b. The flexible band 100 includes a non-stretch central portion 110, a first elastic portion 120, a second elastic portion 130, a first non-stretch terminating end portion 140, and a second non-stretch terminating end portion 150.

In an embodiment, the flexible band 100 is formed from a continuous length of a single layer of material of a suitable biocompatible natural or synthetic elastic material, such as neoprene rubber, styrene-butadiene rubber, neoprene-styrene-butadiene composite rubber, polyurethane, nylon, spandex, nylon-spandex blend, polyesters, polyamides, cotton-spandex blend, or a combination thereof. In an embodiment, the flexible band 100 is formed from a continuous length of two or more layers of elastic band materials having a core comprising neoprene rubber, styrene-butadiene rubber, neoprene-styrene-butadiene composite rubber, or polyurethane, with a layer of nylon or nylon-spandex laminated onto the outer surface 101a, the inner surface 101b, or both surfaces 101a,101b. In an embodiment, the core has a thickness of 1.5 to 3.0 mm and the flexible band 100 has a total thickness of 2.0 mm to 3.5 mm, and in a further embodiment, the flexible band 100 has a total thickness of 2.0 mm to 3.0 mm. In various embodiments, the flexible band 100 may be formed from the continuous length of the elastic band material with one laminated layer on each surface 101a, 101b by die cutting, scissors, laser-cutting, or other types of cutting known to those with ordinary skill in the art.

In an embodiment, non-stretch portions of the flexible band 100 are formed from woven fabrics that impart the non-stretch physical characteristic. In an embodiment, the stretch or elastic portions of the flexible band 100 are formed from non-woven fabrics, knitted fabrics, or woven fabrics containing spandex that individually or when combined with a suitable core material impart the stretch or elastic physical characteristic.

In an embodiment, the flexible band 100 is made from a plurality of fabric segments mechanically fastened together through common methods such as stitching or adhesive. For example, the non-stretch central portion 110 and the first and second non-stretch terminating end portions 140,150 may be formed from a first non-stretch material, and the first and second elastic portions 120,130 may be formed from an elastic material.

The non-stretch central portion 110 has a first end (not labeled) and an opposite second end (not labeled). A first friction pad 111a positioned on the inner surface 101b, between the first and second ends. The first friction pad 111a is formed from a grip or tacky material, such as silicone or urethane. In an embodiment, the first friction pad 111a is mechanically or chemically attached to the inner surface 101b by an adhesive or stitching.

In an embodiment, the first friction pad 111a is formed from a thin, generally rectangular sheet of silicone rubber. In another embodiment, the first friction pad 111a includes a single longitudinal stripe, multiple longitudinal or vertical stripes, dots, or other patterns, formed by known painting, printing, or spray processes, which chemically or mechanically adheres the first friction pad 111a to the inner surface 101b. In the embodiment in which the first friction pad 111a is formed from the grip or tacky material applied to the inner surface 101b by painting, printing, or spraying, the grip or tacky material infiltrates the inner surface 101b of the central portion 110. The grip or tacky material solidifies and cures at least partially within the central portion 110 of the flexible band 100 by exposure to air, heat, or the addition of a separate catalyst. In an embodiment in which the grip or tacky material is silicone, the silicone is cured by condensation curing in the presence of ambient humidity or by addition curing in the presence of a catalyst; either curing may further include the application of heat. The solidified grip or tacky material imparts non-stretch characteristics to the central portion 110.

Figure 6:
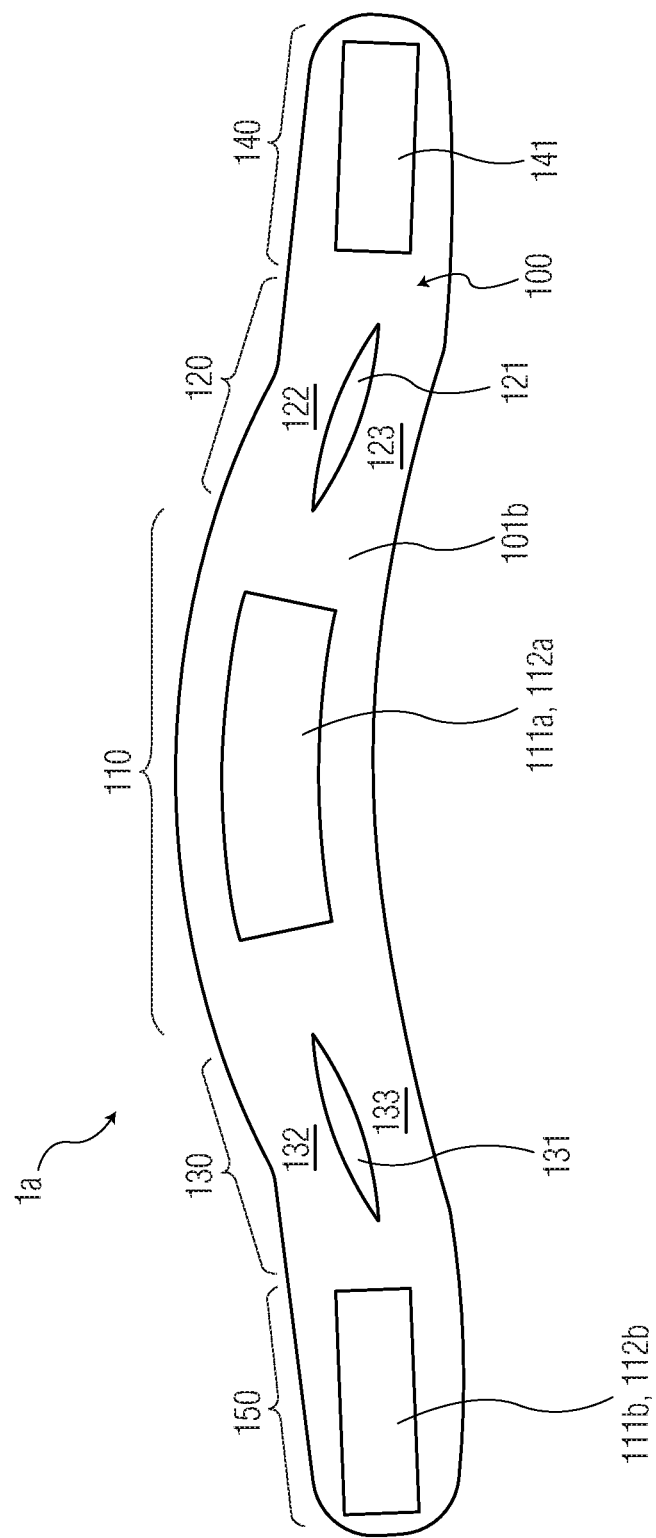
FIG. 6 is a perspective view of an inner facing side of the rear-closing medical headgear.

In an embodiment of FIG. 6, a first non-stretch pad 112a is optionally positioned on the inner surface 101b of the non-stretch central portion 110. The first non-stretch pad 112a is formed from a non-stretch material such as microfiber, or other woven fabrics, which may impart the non-stretch physical property to the non-stretch central portion 110. The first non-stretch pad 112a may be mechanically or chemically attached to the inner surface 101b by stitching or an adhesive.

In an embodiment, the first friction pad 111a is positioned on an outer surface of the first non-stretch pad 112a.

In an embodiment of FIG. 6, a length of the non-stretch central portion 110 is proportional to a length of the first friction pad 111a and/or first non-stretch pad 112a, such that increasing the length of the first friction pad 111a and/or the first non-stretch pad 112a increases the length of the non-stretch central portion 110. Conversely, decreasing the length of the first friction pad 111a and/or the first non-stretch pad 112a decreases the length of the non-stretch central portion 110. In another embodiment, the non-stretching physical properties and length of the central portion 110 are controlled through at least one or more rows of longitudinally extending stitching (not shown), which prevent elastic stretching along the longitudinal axis. In another embodiment, the non-stretching central portion 110 is formed from the first non-stretch material.

In another embodiment, the central portion 110 is made of an elastic material, and therefore stretches under an applied circumferential tensile force across the band. Optionally, the first pad 112a may also be formed from an elastic material, allowing the central portion 110 to maintain elasticity in the presence of the first pad 112a.

The first elastic portion 120 has a terminating end connecting side, and an opposite central portion connecting side extending continuously from the first side of the non-stretch central portion 110 along the longitudinal axis. In an embodiment, when the first elastic portion 120 is formed from the elastic material and the non-stretch central portion 110 is formed from the first non-stretch material, the central portion connecting side of the first elastic portion 120 is mechanically connected to the first side of the non-stretch central portion 110 through an adhesive or stitching.

In an embodiment, the first elastic portion 120 is bifurcated, having a first earcup receiving space 121 positioned along an approximate middle section, an upper strap 122, and a corresponding lower strap 123. The first earcup receiving space 121 is defined by the upper strap 122 and the lower strap 123, having an elastically expandable first diameter. In an embodiment, the first earcup receiving space 121 is a slit extending for a distance along the longitudinal axis and passing through the band 100, and positioned between the upper strap 122 and lower strap 123. In an embodiment, a width of the upper strap 122 and a width of the lower strap 123 are equal. In another embodiment, the widths of the upper strap 122 and lower strap 123 are different. In another embodiment each strap 122,123 displays a unique elastic tension between the straps 122,123.

In an embodiment, the material of one or both of the straps 122,123 is gathered along a substantial mid-portion through a series of stitches (not shown), such that the elastic tension exerted by the straps 122,123 is controlled by the pattern, tightness, and length of stitching of the gathered material. For example, the use of a straight stitching pattern reduces the elastic tension, whereas a zig-zag stitching pattern can maintain the inherent elasticity of the flexible band 100 material. Additionally, the gathered material increases the unexpanded first diameter. Further, the gathered material may assist in retaining the earcups within the first receiving space 121.

In an embodiment, the second elastic portion 130 is complementary and substantially similar to the first elastic portion 120. The second elastic portion 130 has a terminating end connecting side, and a central portion connecting side extending continuously from the second side of the non-stretch central portion 110 along the longitudinal axis. Similar to the first elastic portion 130, in an embodiment, when the second elastic portion 130 is formed from the elastic material and the non-stretch central portion 110 is formed from the first non-stretch material, the central portion connecting side of the second elastic portion 130 is mechanically connected to the second side of the non-stretch central portion 110 through an adhesive or stitching.

The second elastic portion 130 is bifurcated, having a second earcup receiving space 131 positioned along an approximate middle section, an upper strap 132, and a corresponding lower strap 133. The second earcup receiving space 131 is defined by the upper strap 132 and the lower strap 133, having an expandable second diameter. In an embodiment, the second earcup receiving space 131 is a slit extending for a distance along the longitudinal axis and passing through the band 100, and positioned between the upper strap 132 and lower strap 133.

In an embodiment, a width of the upper strap 132 and a width of the lower strap 133 are equal. In another embodiment, the widths of the upper strap 132 and lower strap 133 are different. In another embodiment, each strap 132,133 displays a unique elastic tension between the straps 132,133.

In an embodiment, the material of one or both of the straps 132,133 is gathered along a substantial mid-portion through a series of stitches (not shown), such that the elastic tension exerted by the straps 132,133 is controlled by the pattern, tightness, and length of stitching of the gathered material. For example, the use of a straight stitching pattern reduces the elastic tension, whereas a zig-zag stitching pattern can maintain the inherent elasticity of the flexible band 100 material. Additionally, the gathered material increases the unexpanded second diameter. Further, the gathered material may assist in retaining the earcups within the second receiving space 131.

In an embodiment of FIG. 17, the first elastic portion 120 and second elastic portion 130 extend continuously as unbifurcated portions of fabric from the first side and second side of the central non-stretch portion 110 such that the portions 120,130 may completely cover and retain the earcup 200 (discussed in detail below). In an embodiment, the elastic tension of the first and second elastic portions 120,130 may be controlled by longitudinally extending stitching. Similar to the above-discussed bifurcated embodiments, the elastic tension may be controlled by the pattern, tightness, and length of the longitudinally extending stitching. For example, the use of a straight stitching pattern reduces the elastic tension, whereas a zig-zag stitching pattern can maintain the inherent elasticity of the flexible band 100 material.

In the embodiments of FIGS. 2-8, the first non-stretch terminating end portion 140 has an elastic portion connecting side extending continuously from the terminating end connecting side of the first elastic portion 120, and an opposite terminating end. The first non-stretch terminating end portion 140 includes a first fastener 141 positioned on the inner surface 101b. In another embodiment (not shown), the first fastener 141 is positioned on the outer surface 101a. When the first fastener 141 is positioned on the outer surface 101a, a friction pad (not shown) substantially similar to the first friction pad 111a, may also positioned on the inner surface 101b of the first non-stretch terminating end portion 140.

Attachment of the first fastener 141 imparts the non-stretching physical property to the first terminating end portion 140. A length of the first non-stretch terminating end portion 140 is proportional to a length of the first fastener 141, such that increasing the length of the first fastener 141 increases the length of the first non-stretch terminating end portion 140. Conversely, decreasing the length of the first fastener 141 decreases the length of the first non-stretch terminating end portion 140. Additionally, when the friction pad is positioned on the inner surface 101b, the non-stretching physical property is further enhanced.

In an embodiment, when the first non-stretch terminating end portion 140 is formed from a non-stretch material, the non-stretch material imparts the non-stretching physical property. In an embodiment, the first fastener 141 is a hook and loop style fastener, such as a low-profile hook and loop style fastener, although one of ordinary skill in the art would appreciate that other common fasteners may be used.

In an embodiment, the first terminating end portion 140 is elastic, being formed from an elastic material similar to, or the same as, the elastic material forming the first elastic portion 120. In this embodiment, the first fastener 141 may also be elastic, such as a stretchable hook and loop style fastener.

In another embodiment, a first part of the first terminating end portion 140 is elastic, and a second part of the first terminating end portion 140 is non-stretch. The non-stretch second part may be non-stretch through the use of a non-stretch material, or controlled through the addition of the medical device fastener 300 on the outer surface 101a of the band 100, along the second part of the first terminating end portion 140.

In the embodiments of FIGS. 2-8, the second non-stretch terminating end portion 150 has an elastic portion connecting side extending continuously from the terminating end connecting side of the second elastic portion 130, and an opposite terminating end. In an embodiment, the second non-stretch terminating end portion 150 includes the second fastener 151 positioned on the outer surface 101a. When the second fastener 151 is positioned on the outer surface 101a, a second friction pad 111b, that may be optionally attached to a second non-stretch pad 112b, may be positioned on the inner surface 101b of the second non-stretch terminating end portion 150. In another embodiment (not shown), the second fastener 151 is positioned on the inner surface 101b. Similar to the above-discussed embodiments of the first non-stretch terminating end portion 140, attachment of the second fastener 151 imparts the non-stretching physical property to the second terminating end portion 150. A length of the second non-stretch terminating end portion 150 is proportional to a length of the second fastener 151, such that increasing the length of the second fastener 151 increases the length of the second non-stretch terminating end portion 150. Conversely, decreasing the length of the second fastener 151 also decreases the length of the second non-stretch terminating end portion 150. Additionally, when the second friction pad 111b is positioned on the inner surface 101b, the non-stretching physical property is further enhanced.

In an embodiment, when the second non-stretch terminating end portion 150 is formed from a non-stretch material, the non-stretch material imparts the non-stretching physical property.

In an embodiment, the second fastener 151 is a hook and loop style fastener complementary to the first fastener 141, although one of ordinary skill in the art would appreciate that other common fasteners may be used, so long as the first and second fasteners 141,151 are complementary.

In an embodiment, the second terminating end portion 150 is elastic, being formed from an elastic material similar to, or the same as, the elastic material forming the second elastic portion 130. In this embodiment, the first fastener 141 may also be elastic, such as a stretch hook and loop style fastener.

In another embodiment, a first part of the second terminating end portion 150 is elastic, and a second part of the second terminating end portion 150 is non-stretch. The non-stretch second part may be non-stretch through the use of a non-stretch material, or controlled through the addition of the medical device fastener 300 on the outer surface 101a of the band 100, along the second part of the second terminating end portion 150.

In an embodiment, the first fastener 141 is positioned on a surface opposite to that of the second fastener 151. For example, when the first fastener 141 is positioned on the inner surface 101b, the second fastener 151 is positioned on the outer surface 101a. Conversely, when the first fastener 141 is positioned on the outer surface 101b, the second fastener 151 is positioned on the inner surface 101a.

In an embodiment, the flexible band 100 extends linearly along the longitudinal axis. In another embodiment, the first and second non-stretch terminating end portions 140,150 extend along the longitudinal axis. The non-stretch central portion 110 and first and second elastic portions 120,130 taken together form an arcuate bend extending a distance from the longitudinal axis at an approximate mid-point.

The earcup 200 is a frequency-dependent auditory filter providing sound attenuation generally increasing as a function of frequency, with limited attenuation in the in-utero auditory range. In an embodiment, earcup 200 is a frequency-dependent auditory filter providing sound attenuation that approximates the sound attenuation characteristics of a mother's gravid uterus and abdominal cavity. In an embodiment, each earcup 200 provides at least 12 A-weighted decibels (dBA) of sound attenuation of pink noise. In another embodiment, each earcup 200 provides at least 15 dBA of sound attenuation of pink noise. In another embodiment, each earcup 200 provides at least 20 dBA of sound attenuation of pink noise.

In an embodiment, each earcup 200 provides at least an 8 decibel (dB) noise reduction rating (NRR) or more. In an embodiment, each earcup 200 provides an 8-12 dB NRR. In another embodiment, each earcup 200 provides a 9-11 dB NRR. In an embodiment, each earcup 200 provides at least a 10 dB NRR or more.

In an embodiment, each earcup 200 allows sound frequencies of 300 Hz or less to pass with attenuation less than 10 dB (SPL). In an embodiment, each earcup 200 allows sound frequencies of 400 Hz or less to pass with attenuation less than 10 dB (SPL). In another embodiment, each earcup 200 allows sound frequencies of 500 Hz or less to pass with attenuation less than 10 dB (SPL). In an embodiment, each earcup 200 is a frequency-dependent auditory filter attenuating sounds between 300-500 Hz. In another embodiment, each earcup 200 is a frequency-dependent auditory filter substantially blocking sounds above 2000 Hz. In an embodiment, "substantially blocking" is understood to be at least 98% (17 dB) or more. In another embodiment, "substantially blocking" is understood to be at least 99% (20 dB) or more.

Figure 10:
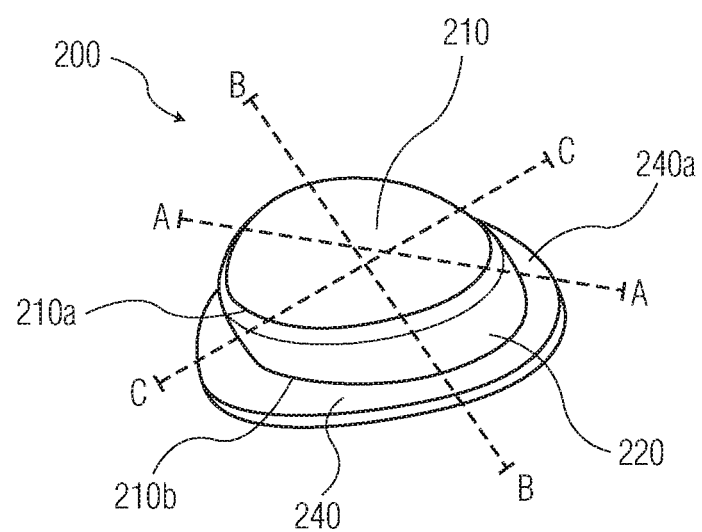
FIG. 10 is an oblique perspective view of an outer surface of the earcup.
Figure 11:
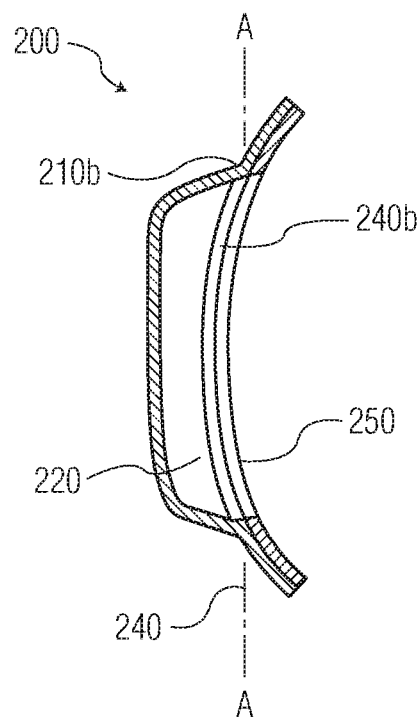
FIG. 11 is a cross-sectional view of the earcup along an A-A line of FIG. 10.
Figure 12:
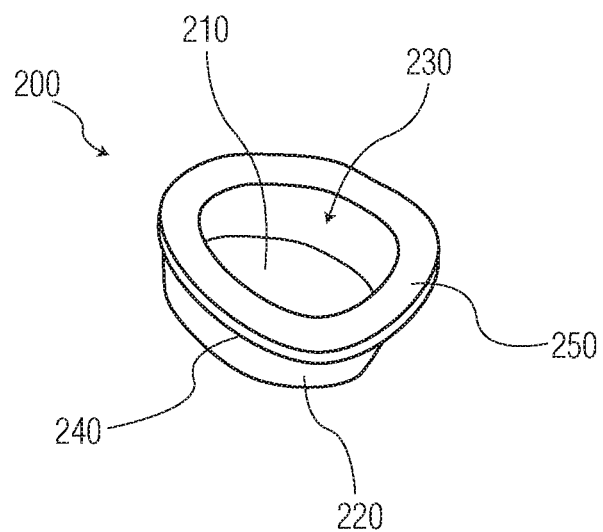
FIG. 12 is an oblique perspective view of an inner surface of the earcup.

In an embodiment of FIGS. 10 and 11, the earcup 200 includes a base 210, a sidewall 220, an ear receiving space 230, a flange 240, and a gasket 250. In an embodiment, the base 210, the sidewall 220, and the flange 240 are referred to as a body of the earcup 200. The earcups 200 are made of a dense polymer, such as polycarbonate, acrylic, ABS, epoxy resin, polyurethane, and silicone, although one of ordinary skill in the art would appreciate that other dense plastics, and sound attenuating materials may also be used. The base 210 is substantially planar, having a general circular or oval-shape and an outer circumferential peripheral edge. In an embodiment, the base 210 is contoured, having a generally convex surface extending outward from the peripheral edge.

In an embodiment, the earcup 200 is optically transparent, enabling areas in and around the ear to be easily examined for evidence of skin breakdown or superficial edema as indicated by a change in color, swelling, bleeding or exudates, without removal of the earcup. In an embodiment, the earcup 200 is optically translucent. In an embodiment, the earcup 200 is optically opaque.

In an embodiment, the base 210 has a thickness of approximately 0.03 inch (0.8 mm) to 0.13 inch (3.2 mm) thick. In another embodiment, the base 210 has a thickness of approximately 0.03 inch (0.8 mm) to 0.08 inch (2.03 mm). In another embodiment, the base 210 has a thickness of approximately 0.06 inch (1.6 mm). The sidewall 220 extends approximately orthogonally from the base 210, having a first sidewall edge 210a continuously connected along the length of the peripheral edge of the base 210, and an opposite second sidewall edge 210b. In an embodiment, the first sidewall edge 210a extends approximately in the same plane as the base 210. In an embodiment, the second sidewall edge 210b is contoured, having a cross-sectional half having a peak on each opposing end and valley disposed therebetween, as seen in the embodiment of FIG. 11.

Taken together, the base 210 and the continuous sidewall 220 form the ear receiving space 230. One of ordinary skill in the art would appreciate that the dimensions of the base 210 and sidewall 220 may be varied to increase or decrease a volume of the ear receiving space 230.

The flange 240 extends radially from a second sidewall edge, having an inner flange contact surface 240b extending orthogonally outward from the second sidewall edge, and an opposite outer flange surface 240a. As seen in the embodiment of FIG. 11, the inner flange contact surface 240b is contoured and complementary to that of the second sidewall edge 210b, having a cross-sectional half with a peak on each opposing end and a valley disposed therebetween. The contoured surface of the flange 240 is complementary to the natural curvature of a head of the newborn, allowing a flange contact surface (not labeled) to form a continuous seal along an entire circumference of the flange 240.

Figure 9:
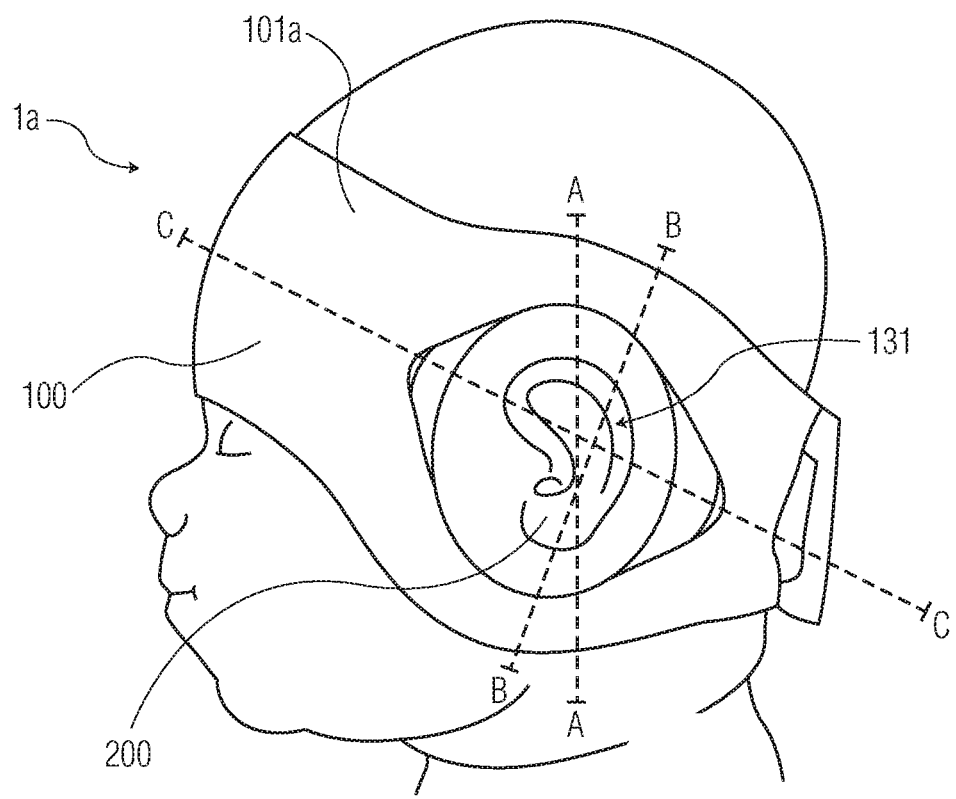
FIG. 9 is a perspective view of a left side of the rear-closing medical headgear positioned on the head of the preterm newborn, and having an earcup.

In the embodiments of FIGS. 9 and 10, a longitudinal axis A extends lengthwise along the earcup 200. A headgear circumferential axis C corresponds to a longitudinal axis of the medical headgear 1 when the earcup 200 is positioned in the earcup receiving space 121,131. A contoured axis B extends substantially orthogonal to the circumferential axis C. The first sidewall edge 210a and/or the inner flange contact surface 240b are generally contoured along opposite edges of the earcup 200 intersecting with the contoured axis B. The contoured first sidewall edge 210a and/or inner flange contact surface 240b have a shape complimentary to the contoured shape of the head of a newborn. In an embodiment, the first sidewall edge 210a and/or inner flange contact surface 240b of the earcup 200 is asymmetrical along the longitudinal axis A.

Figure 2:
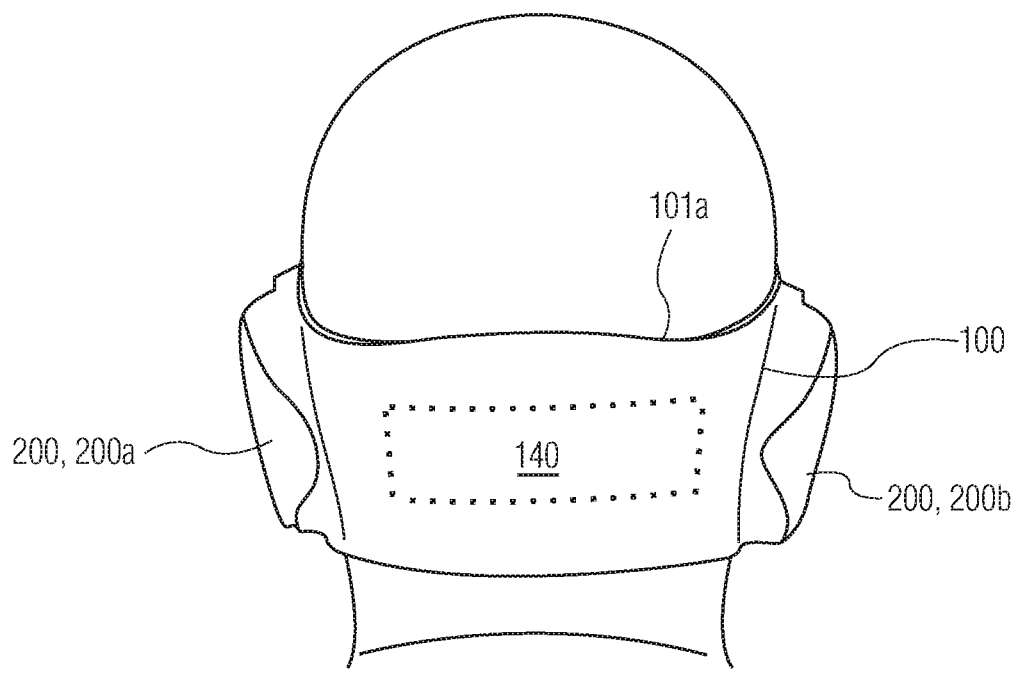
FIG. 2 is a rear perspective view of a rear-closing medical headgear.

In an embodiment of FIG. 2, the earcup 200 is a left-sided earcup 200a having a contoured first sidewall edge 210a and/or inner flange contact surface 240b complimentary to the contoured shape of the head of a newborn surrounding the left ear of the newborn. In an embodiment of FIG. 2, the earcup 200 is a right-sided earcup 200b having a contoured first sidewall edge 210a and/or inner flange contact surface 240b complimentary to the contoured shape of the head of a newborn surrounding the right ear of the newborn. The left-sided earcup 200a is a non-superimposable mirror image of the right-sided earcup 200b, such that the earcups 200a, 200b are chiral with respect to each other.

Figure 13:
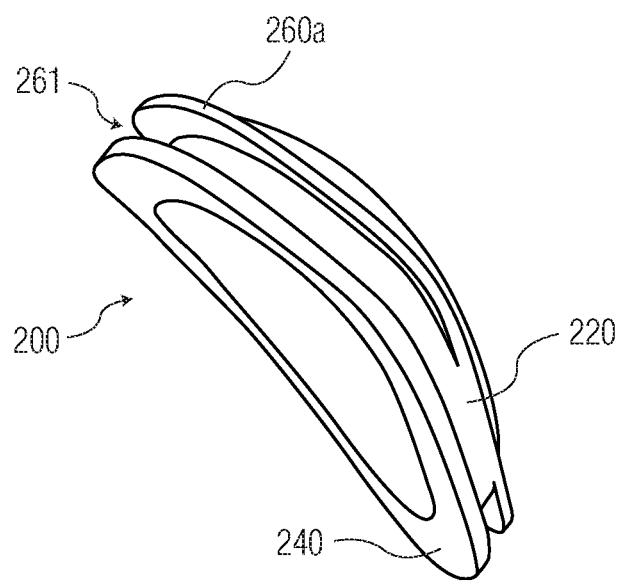
FIG. 13 is a lower oblique perspective view of the earcup having a first outer retaining flange.
Figure 14:
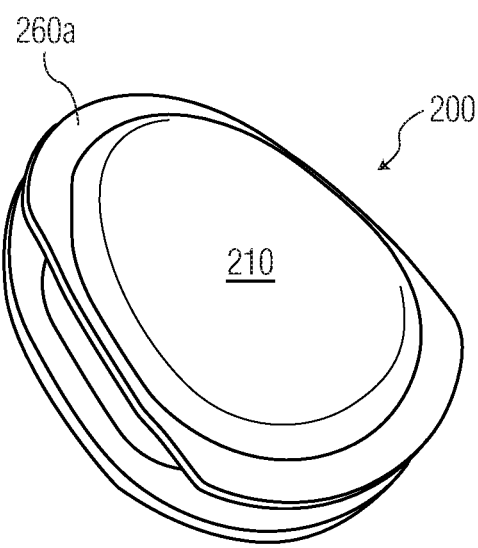
FIG. 14 is an upper oblique perspective view of the earcup in FIG. 13.

In the embodiments of FIGS. 13 and 14, the earcup 200 further includes a first retaining flange 260a disposed continuously and circumferentially on the continuous sidewall 220, between the base 210 and the flange 240. The first retaining flange 260a radially extends outward from the outer surface of the continuous sidewall 200. Taken together, the first retaining flange 260a, the continuous sidewall 200, and the flange 240 form a circumferentially extending band receiving space 261.

Figure 15:
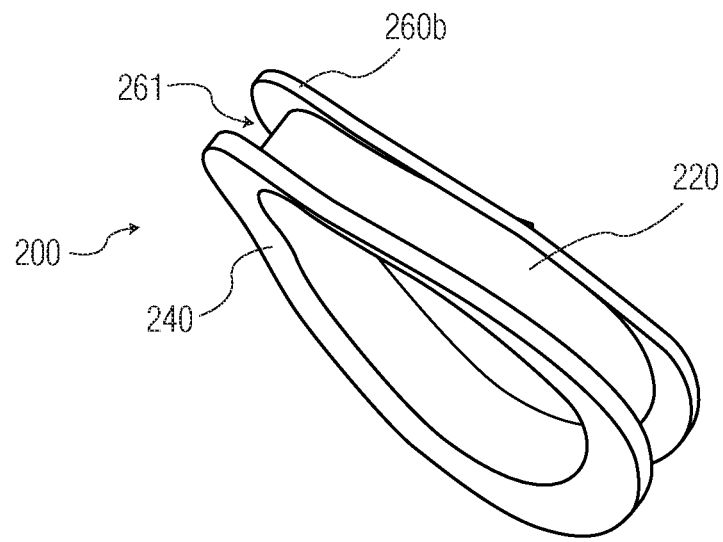
FIG. 15 is a lower oblique perspective view of the earcup having a second outer retaining flange.
Figure 16:
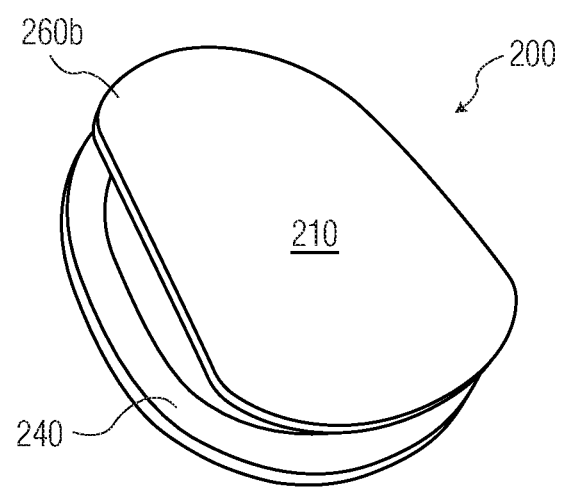
FIG. 16 is an upper oblique perspective view of the earcup in FIG. 15.

In the embodiments of FIGS. 15 and 16, the earcup 200 further includes a second retaining flange 260b disposed continuously and circumferentially on the substantially planar base 210. The second retaining flange 260b radially extends outward from the peripheral edge of the base 210, in approximately the same plane as the surface of the base 210. Taken together, the second retaining flange 260b, the continuous sidewall 200, and the flange 240 form the circumferentially extending band receiving space 261. The gasket 250 is positioned on the flange contact surface of the flange 240, extending continuously along the circumference of the flange contact surface. In an embodiment, the gasket 250 is connected to the flange 240 through an adhesive. The gasket 250 may be made of open or closed-cell foam, such as open-cell urethane foam, or silicone foam. In an embodiment, the gasket 250 is made of an open-cell foam that is breathable, whereby moisture may be able to pass therebetween.

In an embodiment, the gasket 250 has a thickness of 1-6 mm. In an embodiment, the gasket 250 has a thickness of 1-4 mm. In an embodiment, the gasket 250 has a thickness of 2-4 mm. In another embodiment, the gasket 250 has a thickness of 3-6 mm. In another embodiment, the gasket 250 has a thickness of 9 mm. In an embodiment, the gasket 250 has a compression force range for 25% deflection of 0.25-8 psi. In another embodiment, the gasket 250 has a compression force range for 25% deflection of 0.3-3.5 psi.

In an embodiment, when the earcup 200 is made from a flexible material such as silicone rubber, the use of the gasket 250 is optional. When the earcup 200 is used in the absence of the gasket 250, the flange 240 is optionally flexible, allowing the flange 240 to resiliently conform to the contours of a user's head.

In the embodiments of FIGS. 1-8, the plurality of medical device fasteners 300 are positioned on the outer surface 101a of the band 100. In an embodiment, one, two, three, four, or more medical device fasteners 300 are positioned on the outer surface 101a.

Figure 5:
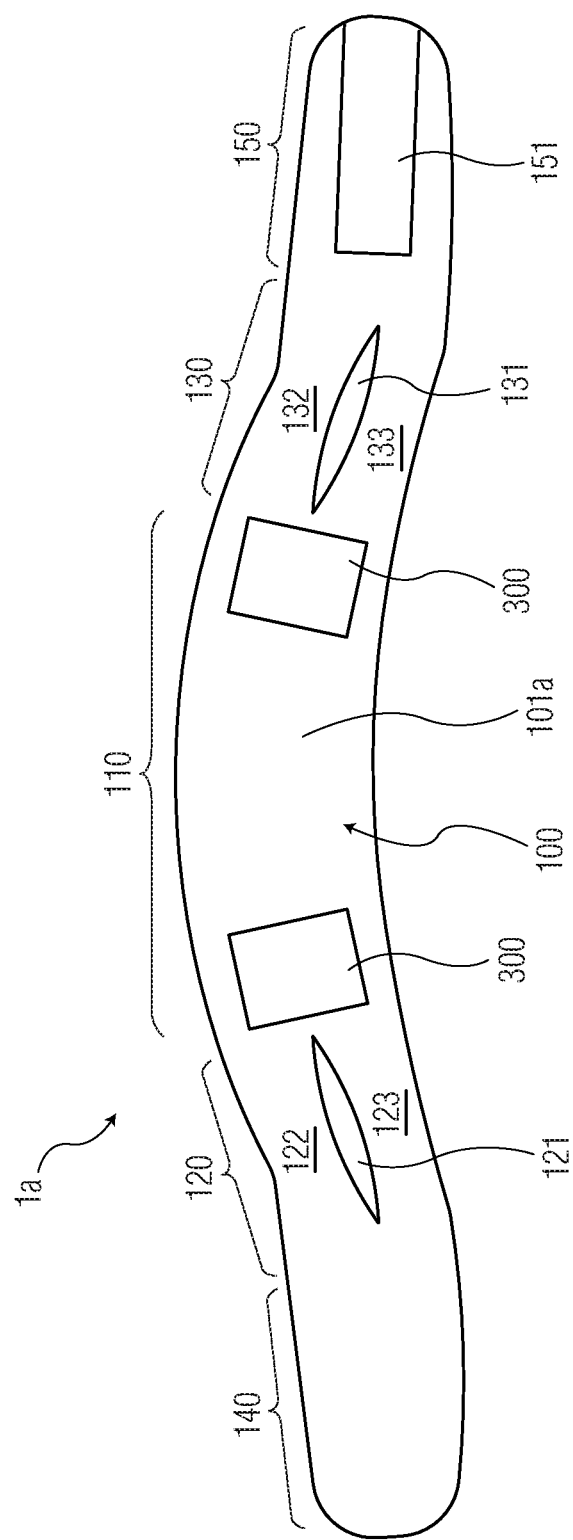
FIG. 5 is a perspective view of an outer facing side of a rear-closing medical headgear.

In the rear-closing embodiments 1a of FIGS. 1 and 5, a pair of medical device fasteners 300 is positioned on the outer surface 101a of the non-stretch central portion 110, with one medical device fastener 300 positioned proximate to the first side, and one medical device fastener 300 positioned proximate to the second side. In another rear-closing embodiment 1*a*, a third medical device fastener 300 is positioned on an approximate mid-portion of the non-stretch central portion 110.

Figure 3:
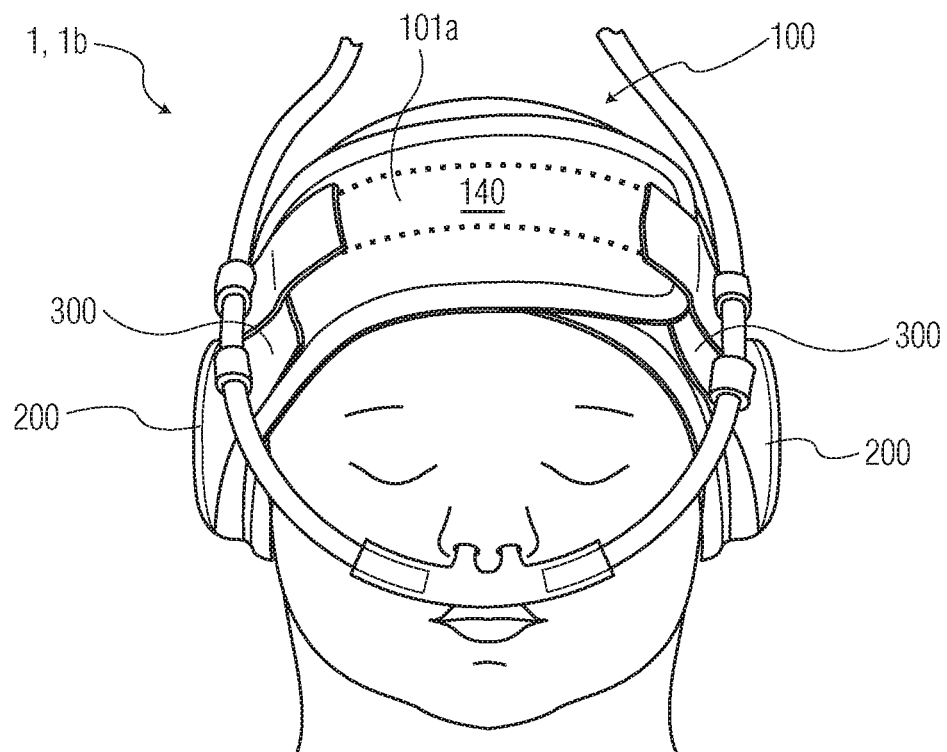
FIG. 3 is a front perspective view of a front-closing medical headgear installed on a head of a preterm newborn.
Figure 4:
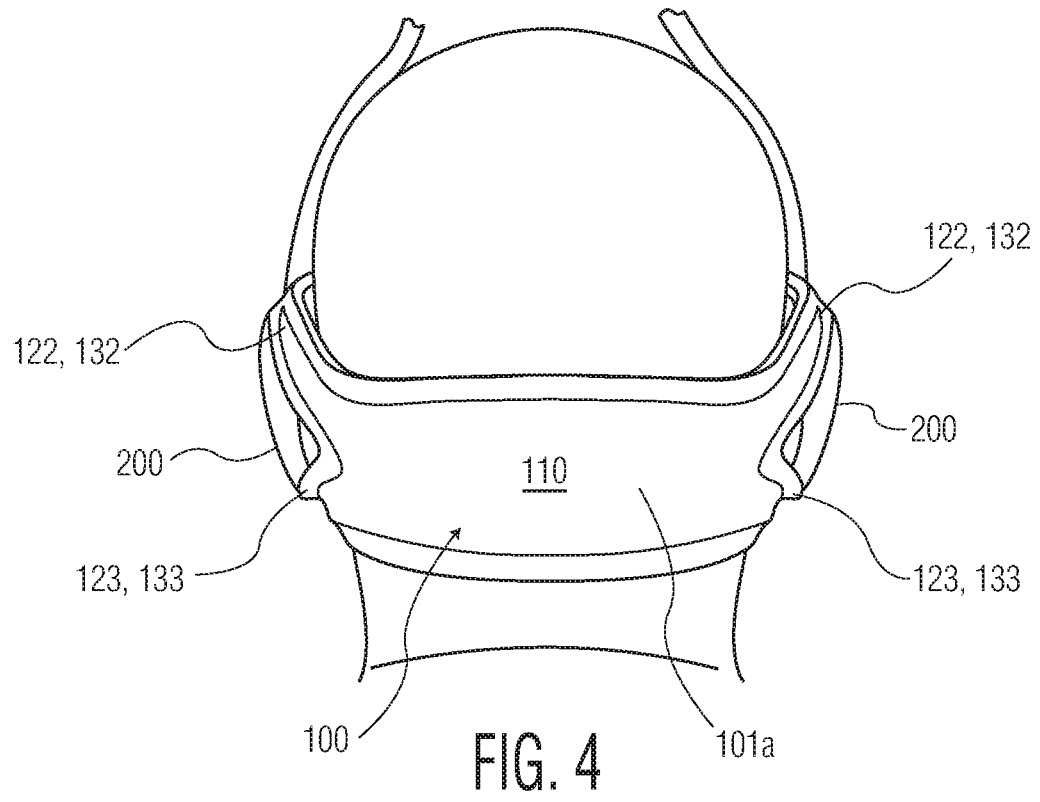
FIG. 4 is a rear perspective view of a front-closing medical headgear.
Figure 7:
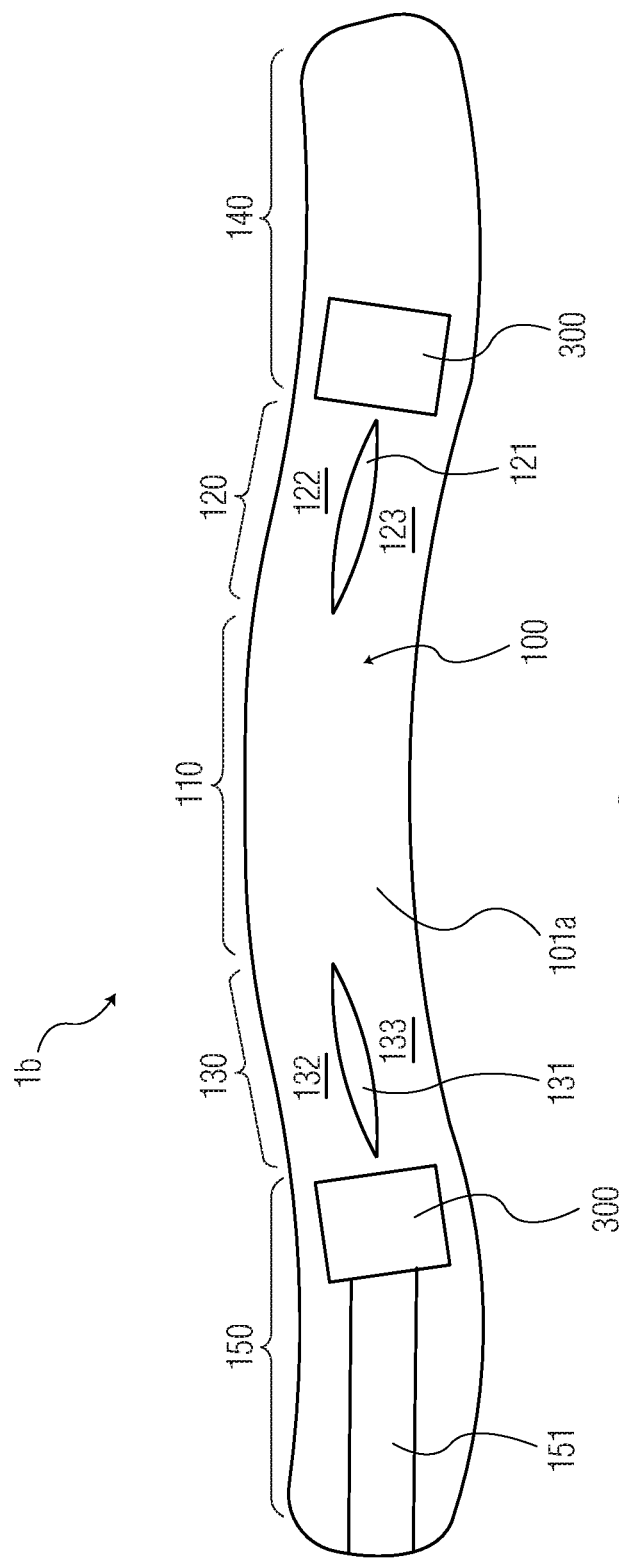
FIG. 7 is a perspective view of an outer facing side of a front-closing medical headgear.

In the front-closing embodiments 1*b* of FIGS. 3 and 7, the pair of medical device fasteners 300 is positioned on the outer surface 101*a* of the non-stretch terminating end portions 140,150. Specifically, one medical device fastener 300 is positioned proximate to the elastic portion connecting side of the first terminating end portion 140, and one medical device fastener 300 is positioned proximate to the elastic portion connecting side of the second terminating end portion 150. In another front-closing embodiment 1*b*, a third medical device fastener 300 is positioned on an approximate mid-portion of the outer surface 101*b* of the first or second terminating end portions 140.

In an embodiment, a removable eyeshade (not shown) may be connected to the band 100 to modify or control the visual environment of a user newborn. The eyeshade may be connected by a hook and loop fastener or any other suitable fastening mechanism known to those of ordinary skill in the art. In an embodiment, the eyeshade is substantially similar to the removable eyeshade described in U.S. Pat. No. 7,878,968 issued to Wittmann-Price et al., with col. 3, lines 52-67 through col. 4, lines 1-8 incorporated herein by reference.

Assembly of the major components and the operation of the medical headgear 1 will now be described.

Each earcup 200 is positioned in the first and second earcup receiving spaces 121,131 by inserting the base 210 and the sidewall 220 through the earcup receiving spaces 121,131 from the inner surface 101*b* towards the outer surface 101*a* of the band 100. As the earcup 200 is positioned in the first earcup receiving space 121, the upper strap 122 and lower strap 123 are elastically displaced, exerting opposing elastic forces against the sidewall 220 to secure the earcup 200 in the first earcup receiving space 121. Similarly, the earcup 200 is positioned in the second earcup receiving space 131.

In the embodiments of FIGS. 13-17, when the earcup 200 is positioned in the first or second earcup receiving spaces 121,131 a portion of the upper straps 122,132 and lower straps 123,133 defining the first and second earcup receiving spaces 121,131 are received in the band receiving space 261.

When the earcup 200 is positioned in the earcup receiving spaces 121,131, the outer flange surface 240*a* contacts the inner surface 101*b* of the band 100, preventing the earcup 200 from being displaced out of an outer surface side of the earcup receiving spaces 121,131 when an outward force is applied to the earcup 200.

Figure 17:
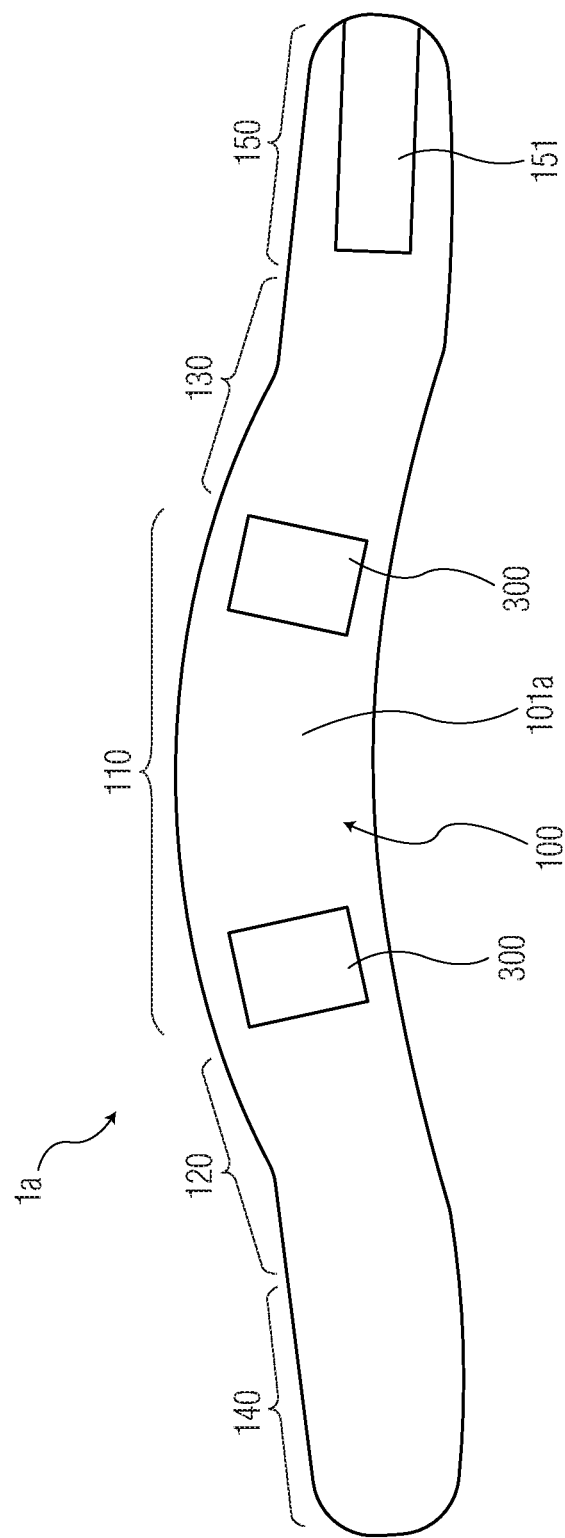
FIG. 17 is a perspective view of an outer facing side of a rear-closing medical headgear.

In the embodiment of FIG. 17, where the first elastic portion 120 and second elastic portion 130 extend continuously as unbifurcated portions of fabric, the outer surface of the ear cup 200 base 210 is positioned against the inner surface 101*b* of the first or second elastic portions 120,130. When an inward force is applied by the band 100, the outer surface of the base 210 contacts the inner surface 101*b*, preventing the earcup 200 from being displaced when an outward force is applied to the earcup 200.

In the rear-closing embodiments 1*a* of FIGS. 1, 2, 5, and 6, the inner surface 101*b* and first friction pad 111*a* of the non-stretch central portion 110 are positioned against the forehead, or higher on the frontal cranial bones anterior to the anterior fontanelle of a newborn. The earcups 200 in the first and second earcup receiving spaces 121,131 are positioned over the ears of the newborn, such that the ears extend into the ear receiving space 230. The upper and lower straps 122,132/123,133 of the first and second elastic portions 120,130 flank upper and lower portions of the ear, applying opposing inward elastic forces on the outer flange surface 240*a*, driving the inner flange surface 240*b* towards the head, compressing the gasket 250, and ultimately forming a seal between the earcups 200 and the head of the newborn.

In an embodiment (not shown, but discussed above), the inner surface 101*b* of the first non-stretch terminating end portion 140 is positioned against a nape of the neck, around a base of the head. In an embodiment, the friction pad positioned on the inner surface 101*b* of the first non-stretch terminating end portion 140 also contacts the nape of the neck. The second fastener 151 on the inner surface 101*b* of the second non-stretch terminating end portion 150 is positioned over the outer surface 101*a* of the first non-stretch terminating end portion 140, such that the second fastener 151 contacts and detachably engages the first fastener 141 on the outer surface 101*b* of the first non-stretch terminating end portion 140.

In an embodiment of FIG. 6, the inner surface 101*b* of the second non-stretch terminating end portion 150 is positioned against the nape of the neck, around the base of the head. Optionally, the friction pad may be positioned on the inner surface 101*b* and also contacts the nape of the neck. The first fastener 141 and the inner surface 101*b* of the first non-stretch terminating end portion 140 are positioned over the outer surface 101*b* of the second non-stretch terminating end portion 150, such that the first fastener 141 contacts and detachably engages the second fastener on the outer surface 101*b* of the second non-stretch terminating end portion 150.

In the front-closing embodiments 1*b* of FIGS. 3, 4, 7, and 8, the inner surface 101*b* and first friction pad 111*a* of the non-stretch central portion 110 are positioned against the nape of the neck, around the base of the head. The earcups 200 in the first and second earcup receiving spaces 121,131 are positioned over the ears of the newborn, such that the ears extend into the ear receiving space 230. The upper and lower straps 122,132/123,133 of the first and second elastic portions 120,130 flank upper and lower portions of the ear, applying opposing inward elastic forces on the outer flange surface 240*a*, driving the inner flange surface 240*b* towards the head, compressing the gasket 250, and ultimately forming a seal between the earcups 200 and the head of the newborn.

Figure 8:
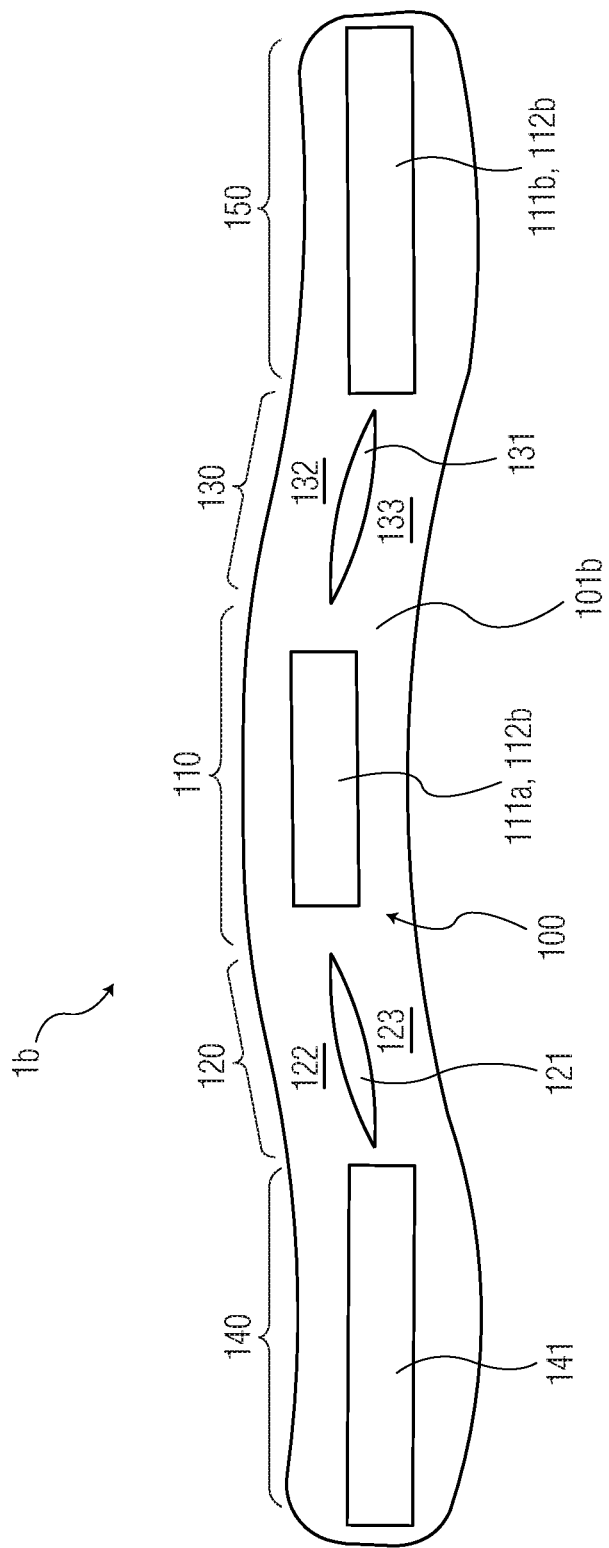
FIG. 8 is a perspective view of an inner facing side of the front-closing medical headgear.

In an embodiment of FIG. 8, the inner surface 101*b* and the second friction pad 111*b* of the second non-stretch terminating end portion 150 are positioned against the forehead, or higher on the frontal cranial bones anterior to the anterior fontanelle. The first fastener 141 on the inner surface 101*b* of the first non-stretch terminating end portion 140 is positioned over the outer surface 101*a* of the second non-stretch terminating end portion 150, such that the first fastener 141 contacts and detachably engages the second fastener 151 on the outer surface 101*b* of the second non-stretch terminating end portion 150.

In an embodiment (not shown but discussed above), the inner surface 101*b* and the friction pad of the first non-stretch terminating end portion 140 are positioned against the forehead, or higher on the frontal cranial bones anterior to the anterior fontanelle. The second fastener 151 on the inner surface 101*b* of the second non-stretch terminating end portion 150 is positioned over the outer surface 101*a* of the first non-stretch terminating end portion 140, such that the second fastener 151 contacts and detachably engages the first fastener 141 on the outer surface 101*b* of the first non-stretch terminating end portion 140.

A compressive force generated by the medical headgear 1 against the head is distributed across the non-stretch central portion 110, first non-stretch terminating end portion 140, and second non-stretch terminating end portion 150. Since the first and second elastic portions 120,130 are the sole elastic portions on the medical headgear 1, a compressive force may be generated directly over to the earcups 200 through a circumferential tensile force applied across the band 100. The compressive force is therefore specifically isolated against the earcup 200, contributing to the formation of the seal between the earcup 200 and the head, while being generally dispersed over the larger area of the non-stretch portions 110,140,150.

In an embodiment, the bifurcated medical headgear 1 is optionally used in the absence of the earcups 200. When the bifurcated headgear 1 is positioned on the head of the newborn, as described above, each ear of the newborn is positioned in the first or second earcup receiving spaces 121,131, extending outward therethrough.

In an embodiment of FIG. 17, where the first elastic portion 120 and the second elastic portion 130 extend continuously as unbifurcated portions of fabric, the medical headgear 1 is optionally used in the absence of the earcups 200. When the unbifurcated headgear 1 is positioned on the head of a newborn, as described above, the inner surfaces 101*b* of the first or second elastic portions 120,130 are positioned directly against the ears of a newborn in the absence of the earcups 200. Additionally, when the unbifurcated medical headgear 1 is positioned on the head of a newborn, as described above, the inner surfaces 101*b* of the first or second elastic portion 120,130 are positioned against the head, above the ears of the newborn in the absence of the earcups 200.

Another front closing embodiment 1*b* of the medical headgear 1 is shown in FIGS. 18-21. Like reference numbers indicate like elements and only the differences with respect to the other embodiments will be described in detail herein.

Figure 18:
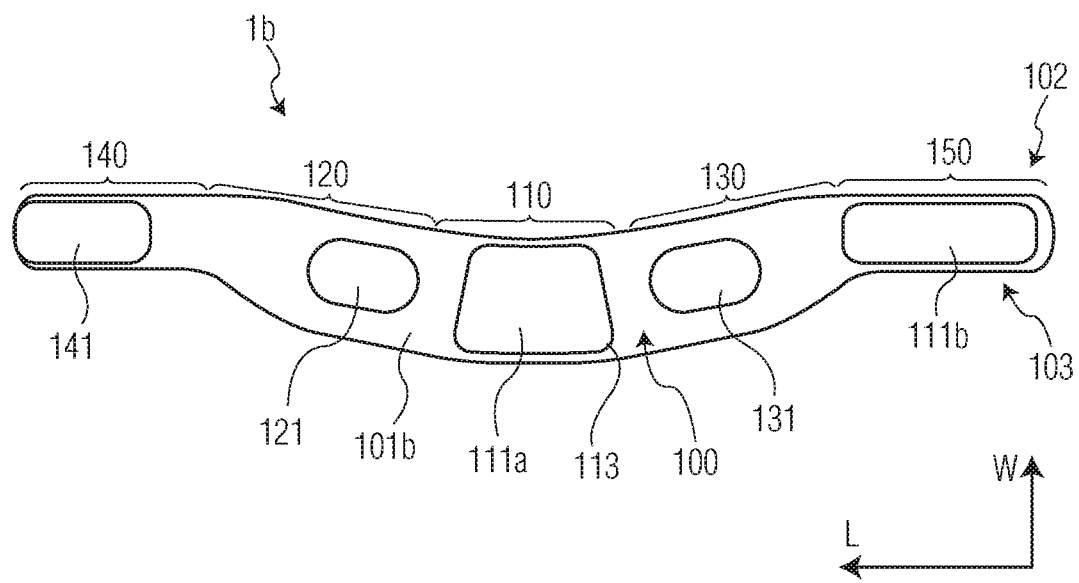
FIG. 18 is a plan view of an inner facing side of a front-closing medical headgear.

As shown in the embodiment of FIG. 18, the first friction pad 111*a* is disposed directly on the inner surface 101*b* of the flexible band 100. The first friction pad 111*a* includes a non-stretch layer 111*a*-1 and a friction layer 111*a*-2 in the embodiment of FIGS. 18-20; the application of the first friction pad 111*a* to the central portion 110 will now be described in detail with reference to FIGS. 18 and 20. The below description applies equally to the application of the second friction pad 111*b* to the second non-stretch terminating end portion 150.

As described in the embodiments above, the first friction pad 111*a* can be formed from a grip or tacky material, such as silicone or urethane, applied to the inner surface 101*b* by painting, printing, or spraying. The embodiment of FIGS. 18-20 will be described with reference to silicone but the description applies equally to urethane and other grip or tacky materials that exhibit the properties described herein.

Figure 20:
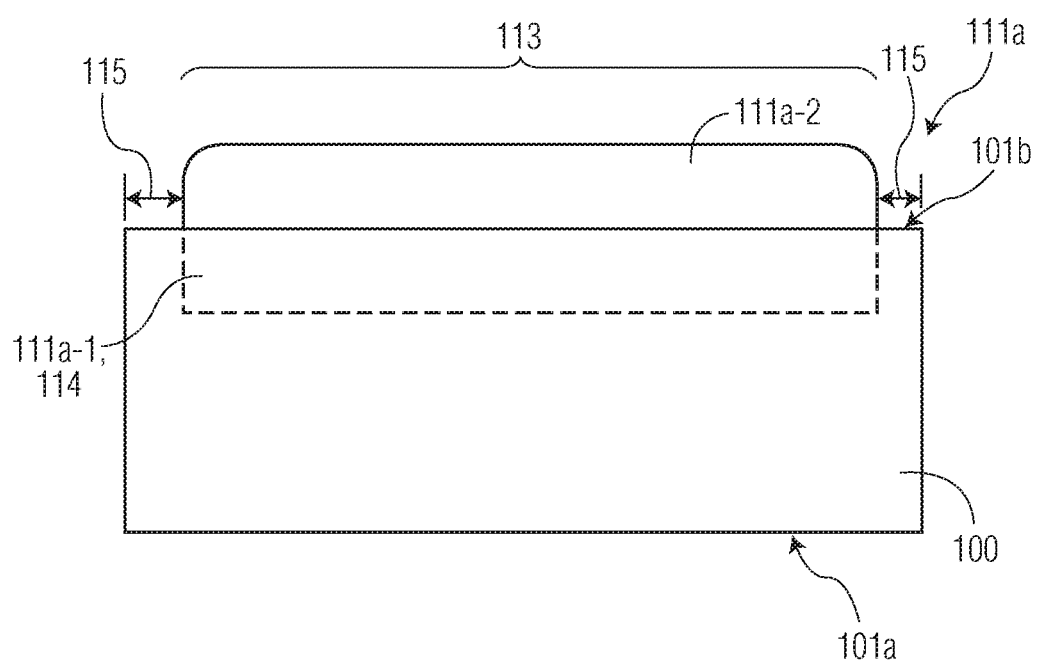
FIG. 20 is a sectional view of the front-closing medical headgear of FIG. 18.

In the embodiment shown in FIGS. 18 and 20, a non-stretch layer 111*a*-1 of silicone is applied in a liquid state directly on a defined area 113 of the inner surface 101*b* in the non-stretch central portion 110 of the flexible band 100. As shown in FIGS. 18 and 20, each of two opposite sides of the defined area 113 are spaced apart from a respective upper side 102 or lower side 103 of the central portion 110 by a friction pad distance 115. The friction pad distance 115, in an embodiment, is 1 mm to 5 mm. In an alternative embodiment, the friction pad distance 115 is zero and the defined area 113 extends fully to the upper side 102 and lower side 103 of the central portion 110. In an embodiment, the defined area 113 may be delineated by a stencil or screen for the painting, printing, or spraying application processes in which the liquid silicone is spread by a squeegee or knife blade. In another embodiment, the defined area 113 may be created manually by the user executing the painting, printing, or spraying application process.

The non-stretch layer 111*a*-1, being in a liquid state at application, infiltrates the inner surface 101*b* and at least partially mixes with the material of the flexible band 100 within the inner surface 101*b*, as shown in FIG. 20. In various embodiments, the non-stretch layer 111*a*-1 can mix with a material of the core of the flexible band 100 and/or with a nylon layer laminated onto the core. The non-stretch layer 111*a*-1 solidifies and cures at least partially within the central portion 110 of the flexible band 100 by exposure to air, heat, or the addition of a separate catalyst. In an embodiment in which the grip or tacky material is silicone, the silicone is cured by condensation curing in the presence of ambient humidity or by addition curing in the presence of a catalyst; either curing may further include the application of heat. The non-stretch layer 111*a*-1 imparts non-stretch characteristics to a non-stretch composite region 114 in which the non-stretch layer 111*a*-1 has solidified; the non-stretch composite region 114 can include a part of a core of the flexible band 100 and/or a part of a nylon layer laminated onto the core. In contrast to the embodiment described above with reference to the first friction pad 111*a* of FIGS. 6 and 8, the non-stretch layer 111*a*-1 of the embodiment of FIGS. 18-20 does not entirely form the first friction pad 111*a* and, as shown in FIG. 20, is approximately flush with the inner surface 101*b* after solidification.

The friction layer 111*a*-2 of silicone is applied in a liquid state directly on the non-stretch composite region 114 in the defined area 113, as shown in FIG. 20. The friction layer 111*a*-2 is confined to the defined area 113 at liquid application in a same manner as the non-stretch layer 111*a*-1. The friction layer 111*a*-2 solidifies and cures by exposure to air, heat, or the addition of a separate catalyst. In an embodiment in which the grip or tacky material is silicone, the silicone is cured by condensation curing in the presence of ambient humidity or by addition curing in the presence of a catalyst; either curing may further include the application of heat. The solidified grip or tacky material of the friction layer 111*a*-2 forms a remainder of the first friction pad 111*a*. In an embodiment, the friction layer 111*a*-2 protrudes from the inner surface 101*b* by a distance of approximately 0.5 mm. As shown in FIG. 20, the exterior edge of the friction layer 111*a*-2, and thereby the exterior edge of the first friction pad 111*a*, has a rounded profile upon solidification and curing. In another embodiment, the exterior edge of the friction layer 111*a*-2 and the first friction pad 111*a* may have a right angle corner profile.

In an alternative embodiment, the non-stretch layer 111*a*-1 and the friction layer 111*a*-2 are applied together in a single liquid state application directly on the defined area 113 of the inner surface 101*b* in the non-stretch central portion 110 of the flexible band 100. In further alternative embodiments, the friction layer 111*a*-2 is formed from a separately solidified and cured piece of silicone. In an embodiment, the friction layer 111*a*-2 is cut from a continuous sheet of silicone to a size matching the dimensions of the defined area 113. In another embodiment, the friction layer 111*a*-2 is formed in a mold to have a solidified and cured size matching the dimensions of the defined area 113. The separately formed friction layer 111*a*-2 is then bonded to the non-stretch composite region 114 by applying a layer of adhesive to at least one of the composite region 114 and the separately formed friction layer 111a-2 and pressing the composite region 114 and friction layer 111a-2 together. In an embodiment, the adhesive is a layer of liquid silicone. In a further alternative embodiment, the separately formed friction layer 111a-2 is attached with the adhesive directly to the inner surface 101b; in this embodiment, the non-stretch layer 111a-1 and composite region 114 are created by the solidification and curing of the adhesive applied to the friction layer 111a-2.

In the embodiment shown in FIGS. 18-21, the first fastener 141 is a hook and loop style fastener and the second fastener 151 is formed by the outer surface 101a of the flexible band 100. In an exemplary embodiment, the first fastener 141 is a low profile hook fastener which engages loops of a layer of nylon material laminated to form the outer surface 101a.

In the embodiment shown in FIGS. 18-21, the earcup receiving spaces 121, 131 have an approximately oval shape and are die cut into the elastic portions 120, 130 of the flexible band 100.

Figure 19:
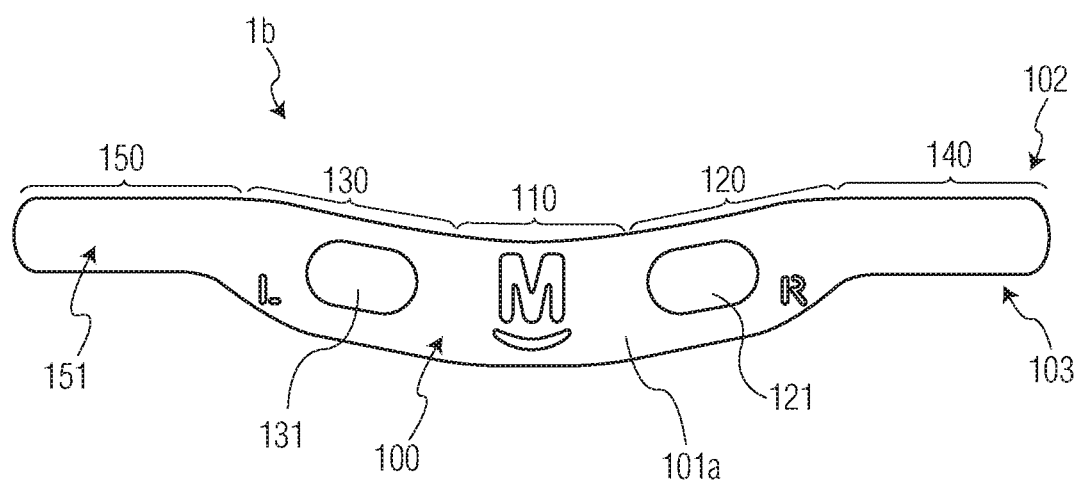
FIG. 19 is a plan view of an outer facing side of the front-closing medical headgear of FIG. 18.
Figure 21:
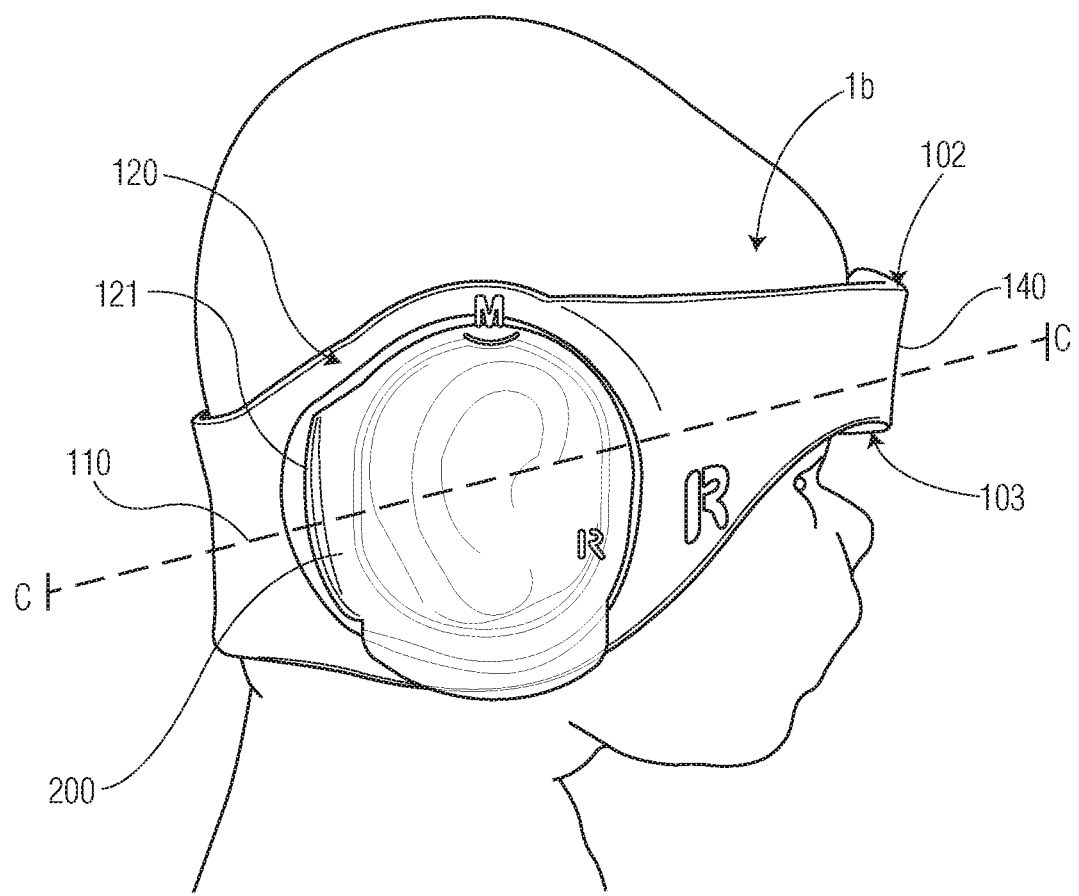
FIG. 21 is a side view of the front-closing medical headgear of FIG. 18 positioned on the head of a newborn.

The flexible band 100 has a longitudinal direction L and a width direction W extending perpendicular to the longitudinal direction L. The width direction W, as shown in FIGS. 18, 19, and 21, extends between an upper side 102 and a lower side 103 of the flexible band 100. In the embodiment shown in FIGS. 18-21, the terminating end portions 140, 150 each have a width in the width direction W which is narrower than a width of the elastic portions 120, 130 and a width of the central portion 110 in the width direction W. In the embodiment shown in FIGS. 18, 19 and 21, the terminating end portions 140, 150 each have a width that is 40-80% of the width of the central portion 110. In a further embodiment, the terminating end portions 140, 150 each have a width that is 60-70% of the width of the central portion 110.

In comparison with the embodiment shown in FIGS. 7 and 8, the narrower width of the terminating end portions 140, 150 is taken entirely from the lower side 103 of the flexible band 100 in the embodiment of FIGS. 18-21; that is, the upper side 102 of the flexible band 100 in FIGS. 18-21 has a same position relative to the elastic portions 120, 130 and central portion 110 as the flexible band 100 in FIGS. 7 and 8. As shown in FIG. 21, the narrower width of the terminating end portions 140, 150 allows the front closing medical headgear 1b of the embodiment of FIGS. 18-21 to be positioned with the circumferential axis C having a shallower angle, lower on the forehead of the newborn.

Figure 22:
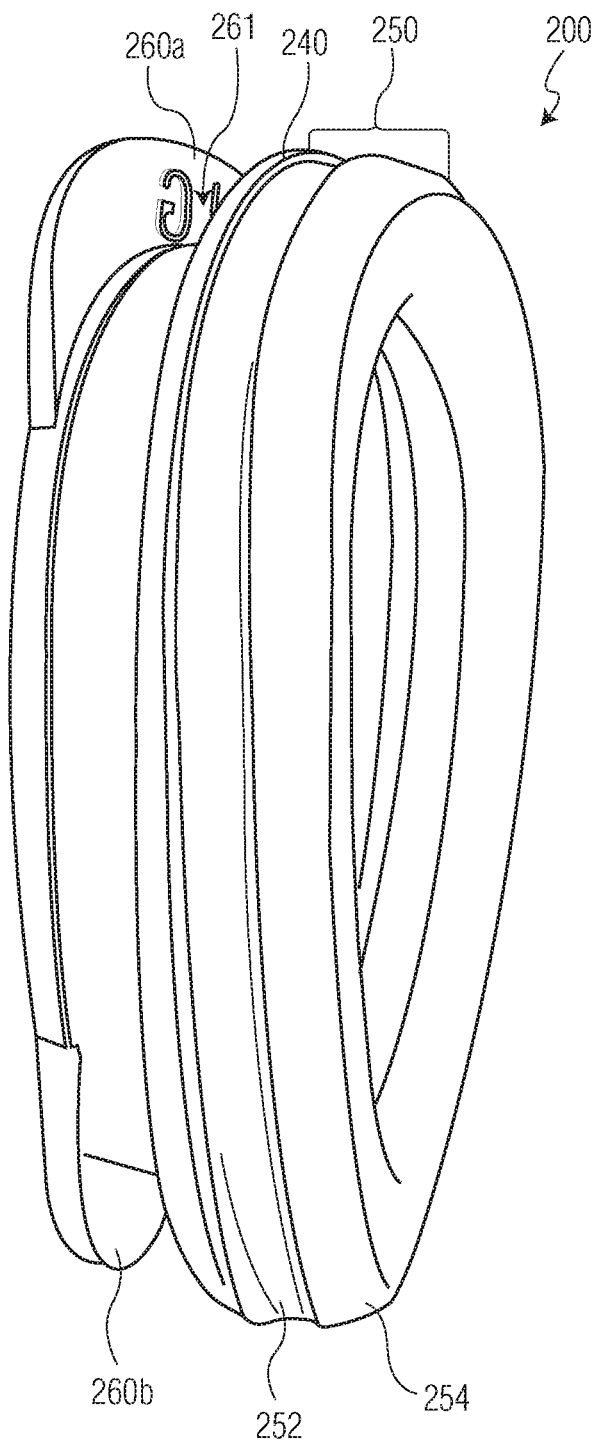
FIG. 22 is a perspective view of an earcup.

An earcup 200 according to another embodiment is shown in FIG. 22. The earcup 200 shown in FIG. 22 has a gasket 250 which includes a first gasket layer 252 and a second gasket layer 254. The first gasket layer 252 is attached to the flange 240 by an adhesive, such as glue or tape. The second gasket layer 254 is attached to a side of the first gasket layer 252 opposite the flange 240 by an adhesive. In an embodiment, the adhesive attaching the first gasket layer 252 to the flange 240 and the second gasket layer 254 to the side of the first gasket layer 252 is a double-side adhesive tape, such as a polyethylene tape with double-sided acrylate adhesive. The adhesive attaching the second gasket layer 254 to the first gasket layer 252 provides a stiffness limiting shear of the combined gasket layers 252, 254 in a plane parallel to a face of the flange 240 but does not impact a combined compressibility of the gasket layers 252, 254 in a direction toward the flange 240.

The first gasket layer 252 and the second gasket layer 254 have a same thickness. In an exemplary embodiment, each of the first gasket layer 252 and the second gasket layer 254 has a thickness of 3 mm and the gasket 250 has a thickness of 6 mm. In the embodiment shown in FIG. 22, the edges of the second gasket layer 254 have a rounded profile.

In other embodiments shown in FIGS. 23-27, the medical headgear 1 includes an overhead strap 400. The overhead strap 400 has an overhead band 410 and a plurality of overhead fasteners 420. The overhead band 410 is formed from a same material as the flexible band 100. In the shown embodiment, each of the overhead fasteners 420 is a hook fastener capable of engaging loops in the material of an outer surface 410a of the overhead band 410 and/or the outer surface 101a of the flexible band 100. In other embodiments, the overhead fasteners 420 may be any type of fabric fasteners known to those with ordinary skill in the art.

Figure 23:
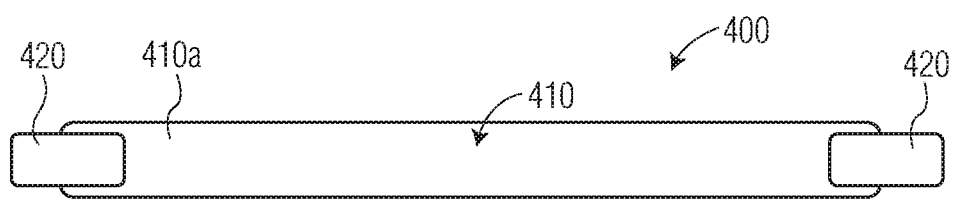
FIG. 23 is a plan view of an overhead strap.
Figure 24:
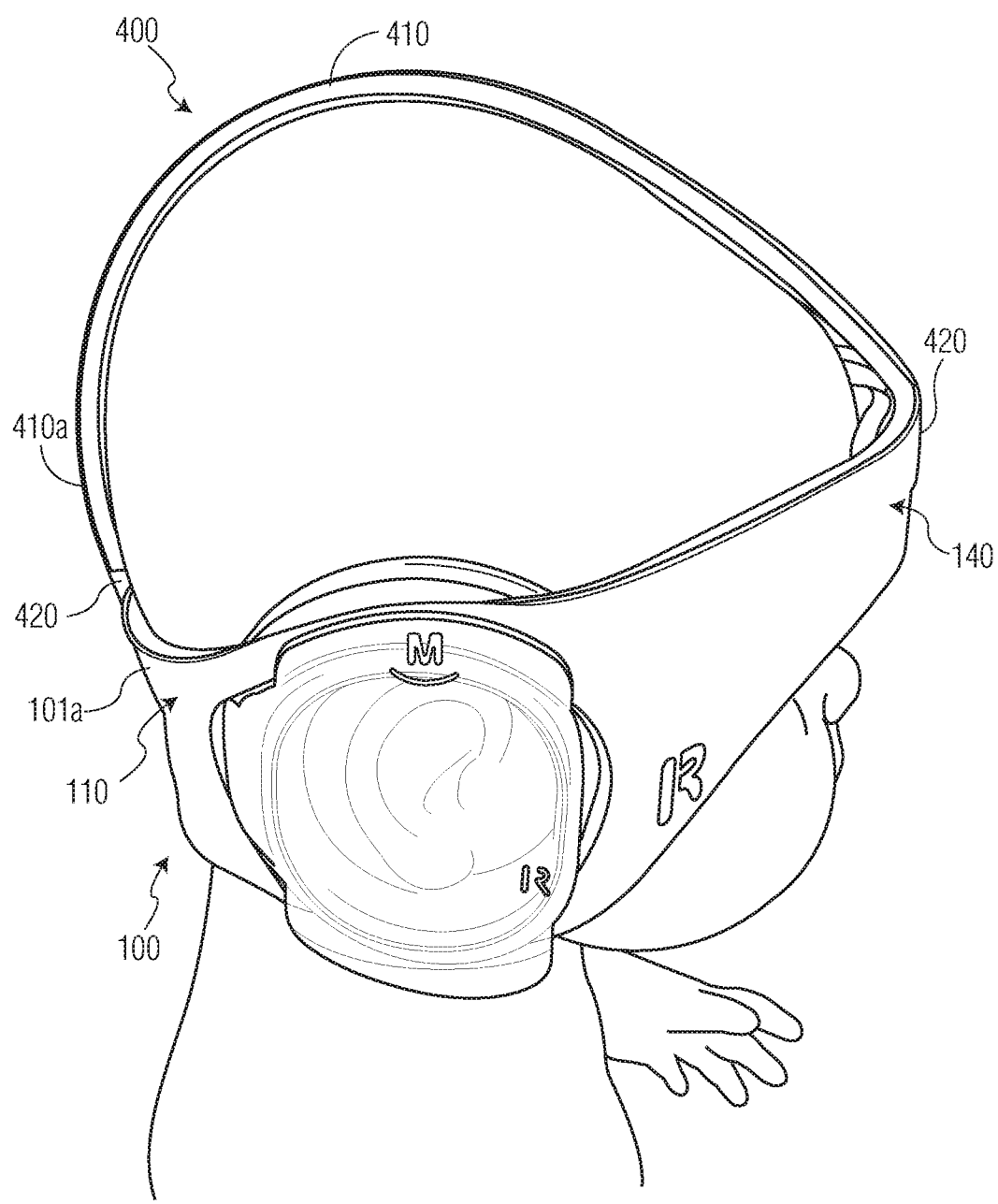
FIG. 24 is a perspective view of the front-closing medical headgear of FIG. 18; positioned on the head of a newborn with the overhead strap of FIG. 23.

In the embodiment shown in FIG. 23, the overhead band 410 has a linear, rectangular shape with one overhead fastener 420 attached to each of two opposite ends of the overhead band 410. As shown in FIG. 24, the overhead fastener 420 at a first end of the overhead band 410 is attached to the outer surface 410a of the overhead band 410 and the outer surface 101a of the flexible band 100 at the central portion 110. The overhead fastener 420 at an opposite second end of the overhead band 410 is attached to the outer surface 410a of the overhead band 410 and the outer surface 101a of the flexible band 100 at the non-stretch terminating end portion 140. The overhead strap 400 extends centrally from front to back over the head of the newborn.

Figure 25:
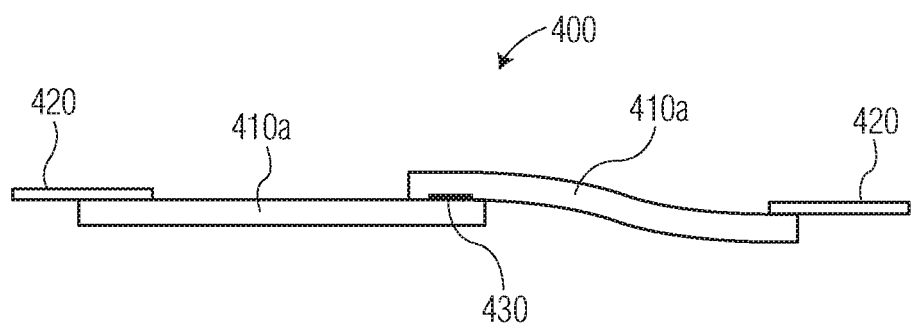
FIG. 25 is a sectional view of an overhead strap.

In another embodiment shown in FIG. 25, the overhead band 410 comprises a plurality of sections 410a held together by additional hook fasteners 430. The plurality of sections 410a are positioned to overlap one another, allowing for adjustment of an overall length of the overhead strap 400.

Figure 26:
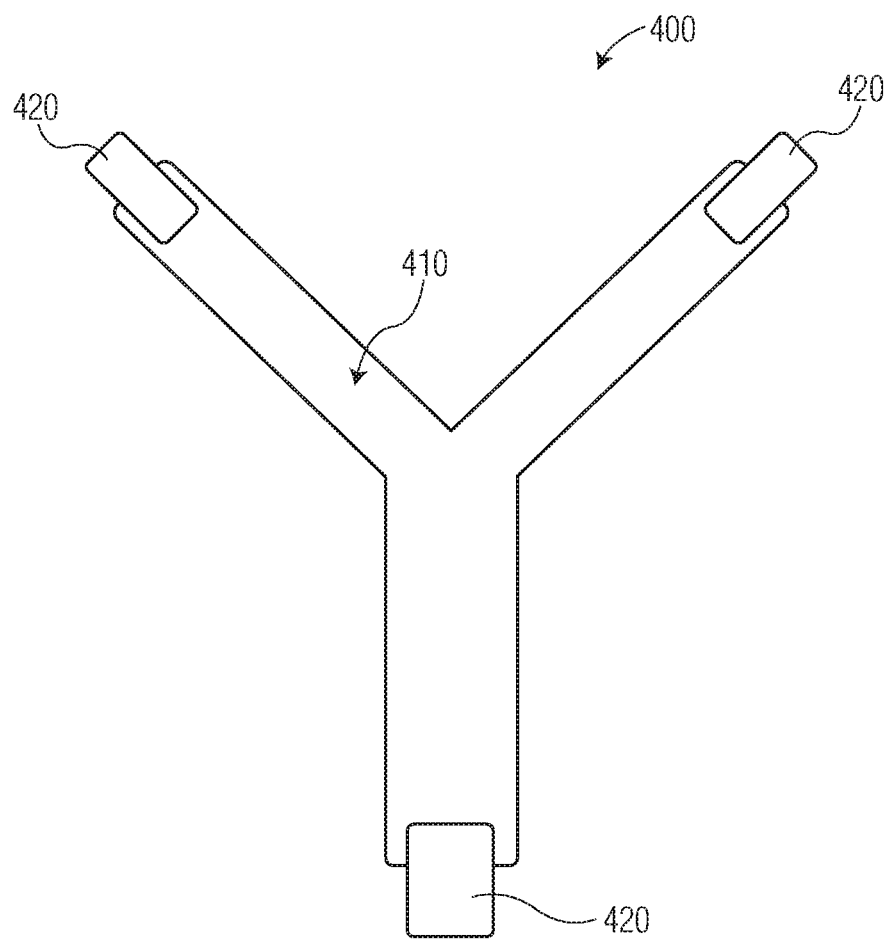
FIG. 26 is a plan view of an overhead strap.
Figure 27:
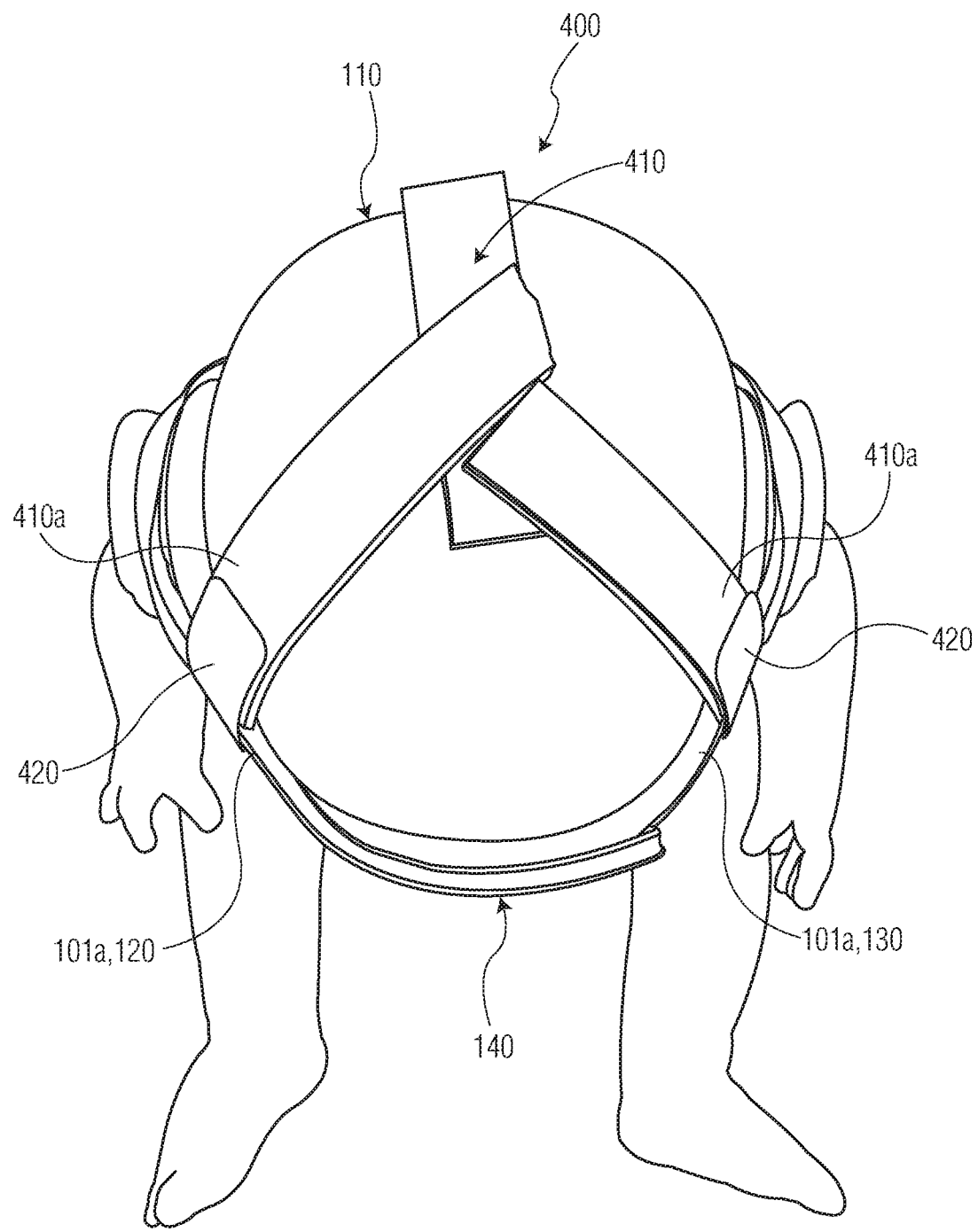
FIG. 27 is a perspective view of the front-closing medical headgear of FIG. 18 positioned on the head of a newborn with the overhead strap of FIG. 26.

In another embodiment shown in FIG. 26, the overhead band 410 has a Y-shape with one overhead fastener 420 positioned on each of the three ends of the overhead band 410. As shown in FIG. 27, the overhead fastener 420 at a first end of the overhead band 410 is attached to the outer surface 101a of the flexible band 100 at the first elastic portion 120, the overhead fastener 420 at a second end of the overhead band 410 is attached to the outer surface 101a of the flexible band 100 at the second elastic portion 130, and the overhead fastener 420 at a third end of the overhead band 410 is attached to the outer surface 101a of the flexible band 100 at the central portion 110. The overhead strap 400 extends over the head of the newborn with an intersection of the Y-shape positioned over the crown of the head. In another embodiment, the overhead strap 400 may be positioned in a reversed orientation with two of the overhead fasteners 420 attached to the central portion 110 and one of the overhead fasteners 420 attached to the non-stretch terminating end portion 140. In a further embodiment, the Y-shaped overhead band 410 may comprise a plurality of linear sections overlapping with one another and attached with additional hook fasteners.

Figure 28:
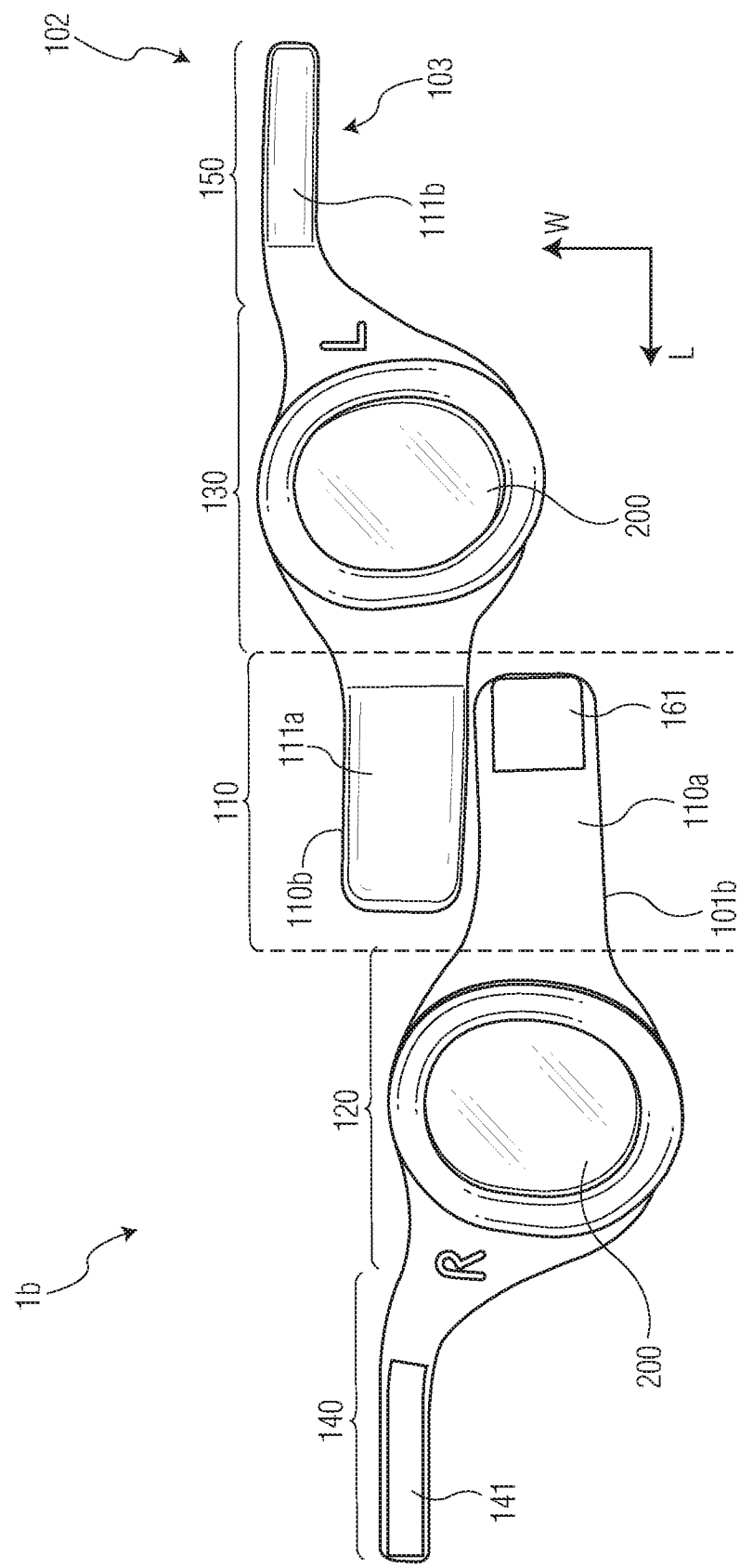
FIG. 28 is a plan view of an inner facing side of a front-closing medical headgear in a separated state.
Figure 29:
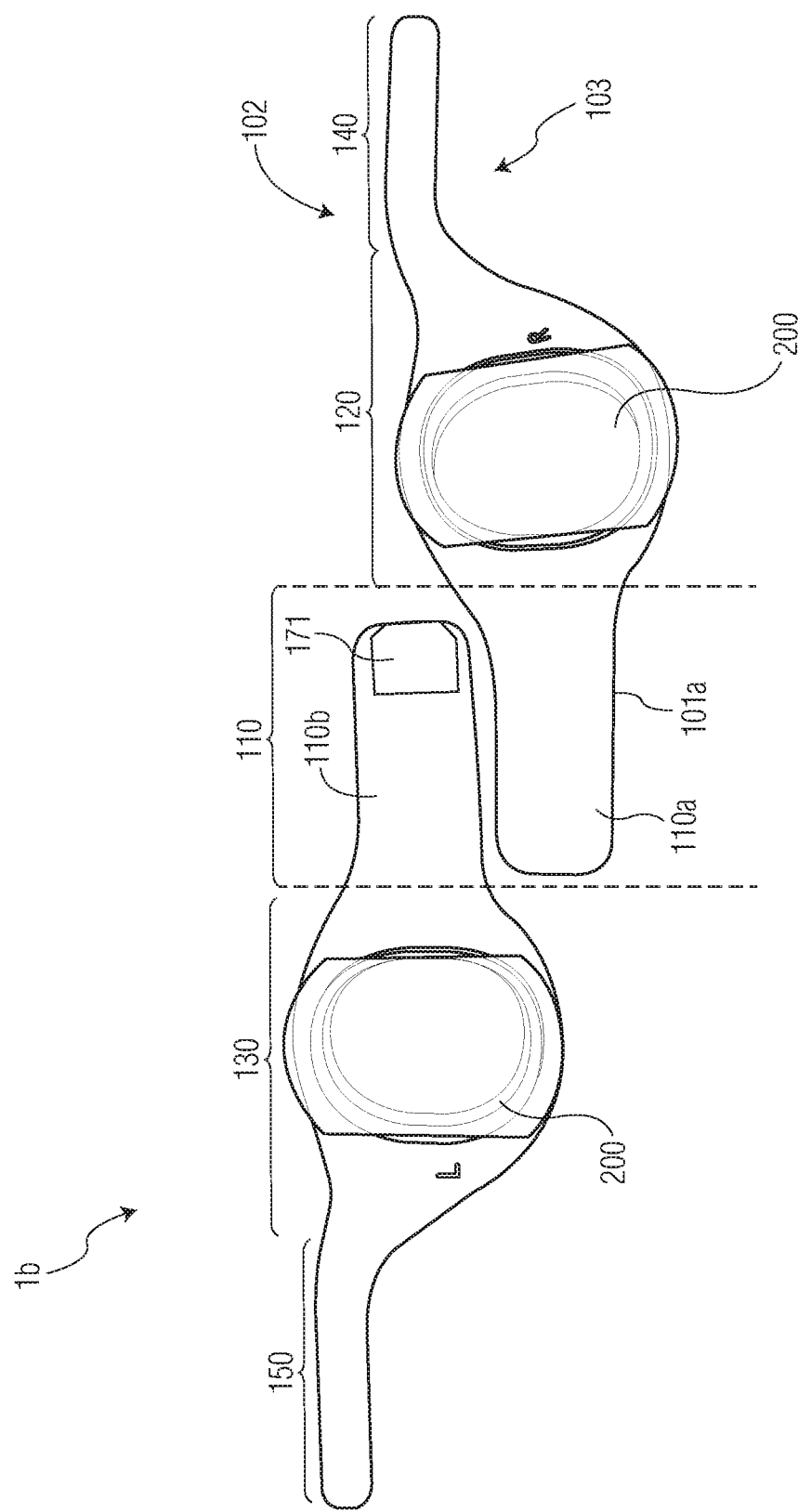
FIG. 29 is a plan view of an outer facing side of the front-closing medical headgear of FIG. 28 in the separated state.
Figure 30:
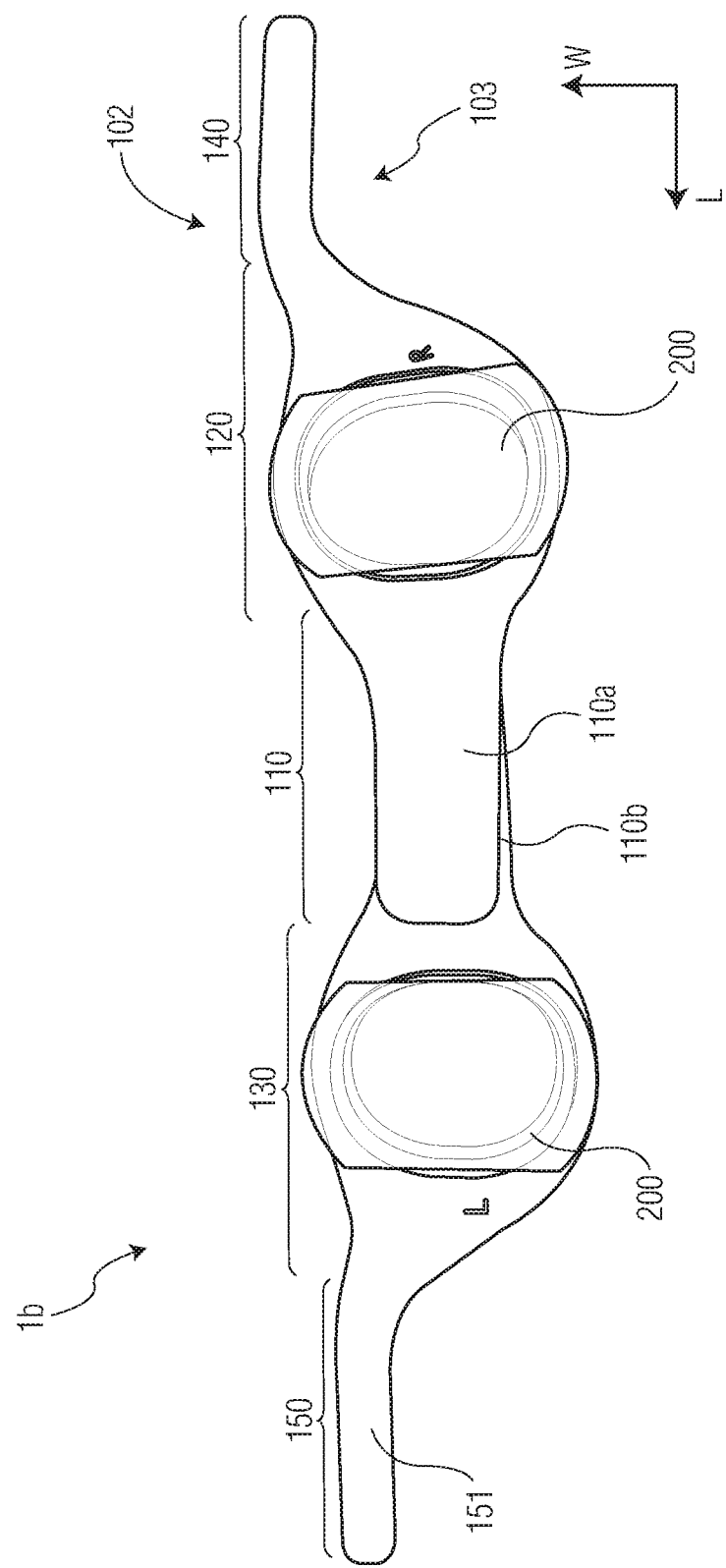
FIG. 30 is a plan view of the outer facing side of the front-closing medical headgear of FIG. 28 in an attached state.

Another front closing embodiment 1b of the medical headgear 1 is shown in FIGS. 28-30. Like reference numbers indicate like elements and only the differences with respect to the other embodiments will be described in detail herein.

In the front closing embodiment 1b shown in FIGS. 28-30, the terminating end portions 140, 150 each have a width that is 30-60% of the width of the central portion 110 in the width direction W, and in a further embodiment, is 40-50% of the width of the central portion 110 in the width direction W. Further, the width of the central portion 110 is narrower than a width of the elastic portions 120, 130.

The central portion 110 in the embodiment of FIGS. 28-30 has a first central portion 110a removably attachable to a second central portion 110b. As shown in FIGS. 28 and 29, the first central portion 110a extends continuously from the central portion connecting side of the first elastic portion 120. The second central portion 110b extends continuously from the central portion connecting side of the second elastic portion 130. The first central portion 110a, as shown in FIG. 28, has a third fastener 161 disposed on the inner surface 101b at an end of the first central portion 110a opposite the first elastic portion 120. The second central portion 110b, as shown in FIG. 29, has a fourth fastener 171 disposed on the outer surface 101a at an end of the second central portion 110b opposite the second elastic portion 130. In an embodiment, the third fastener 161 and the fourth fastener 171 are both hook fasteners and, in a further embodiment, are low profile hook fasteners which engage loops of layers of nylon material laminated to form the outer surface 101a and the inner surface 101b.

As shown in FIG. 30, to form the central portion 110, the first central portion 110a is overlayed on the second central portion 110b. The third fastener 161 on the inner surface 101b of the first central portion 110a engages the outer surface 101a of the second central portion 110b and the fourth fastener 171 on the outer surface 101a of the second central portion 110b engages the inner surface 101b of the first central portion 110a, removably securing the first central portion 110a to the second central portion 110b. The first central portion 110a and the second central portion 110b may be positioned overlaying each other in a range of positions along the longitudinal direction L, varying an overall length of the flexible band 100 in the longitudinal direction L.

The above described embodiments of the medical headgear 1 are suitable for use on preterm newborns, reduce environmental noise to in-utero acoustic levels, and provide a stable support for attaching respiratory support tubes and other medical devices.

For both rear-closing embodiments 1a of FIGS. 1, 2, 5, and 6, and front-closing embodiments 1b of FIGS. 3, 4, 7, 8, 18, 19, and 28-30 the band 100 may be positioned on the head such that the anterior and posterior fontanelles of the newborn are exposed, enabling the fontanelles to be easily examined, for example to inspect the anterior fontanelle for evidence of intraventricular hemorrhage.

While the above embodiments are written in the context of newborns, and more specifically, towards preterm newborns, the medical headgear 1 is not limited to such an application. Rather, one of ordinary skill in the art would appreciate that the scale of the medical headgear 1 can be increased for application in adolescents and adults, without departing from the scope and spirit of the invention.

Additionally, the medical headgear 1 may optionally be used without the earcups 200. Without the earcups 200, the medical headgear 1 may serve as a securing device for attachment of respiratory support tubes or other medical equipment.

The gasket 250, in an embodiment, is formed of a first foam material. The first foam material of the gasket 250, in an embodiment, is an open-cell urethane foam material that has a density of approximately 15 lb/ft$^3$ and a compression force deflection value for 25% deflection of 0.3-3.5 psi. The term "approximately" with reference to the density of the open-cell urethane foam material described herein and described in other embodiments below is defined as +/−10%. In the embodiment shown in FIG. 22, the first gasket layer 252 and the second gasket layer 254 are each formed of the first foam material. In other embodiments, the first foam material can be any open-cell foam material or any closed-cell foam material having the characteristics described herein. In other embodiments, the first foam material can be a silicone foam material.

Figure 31:
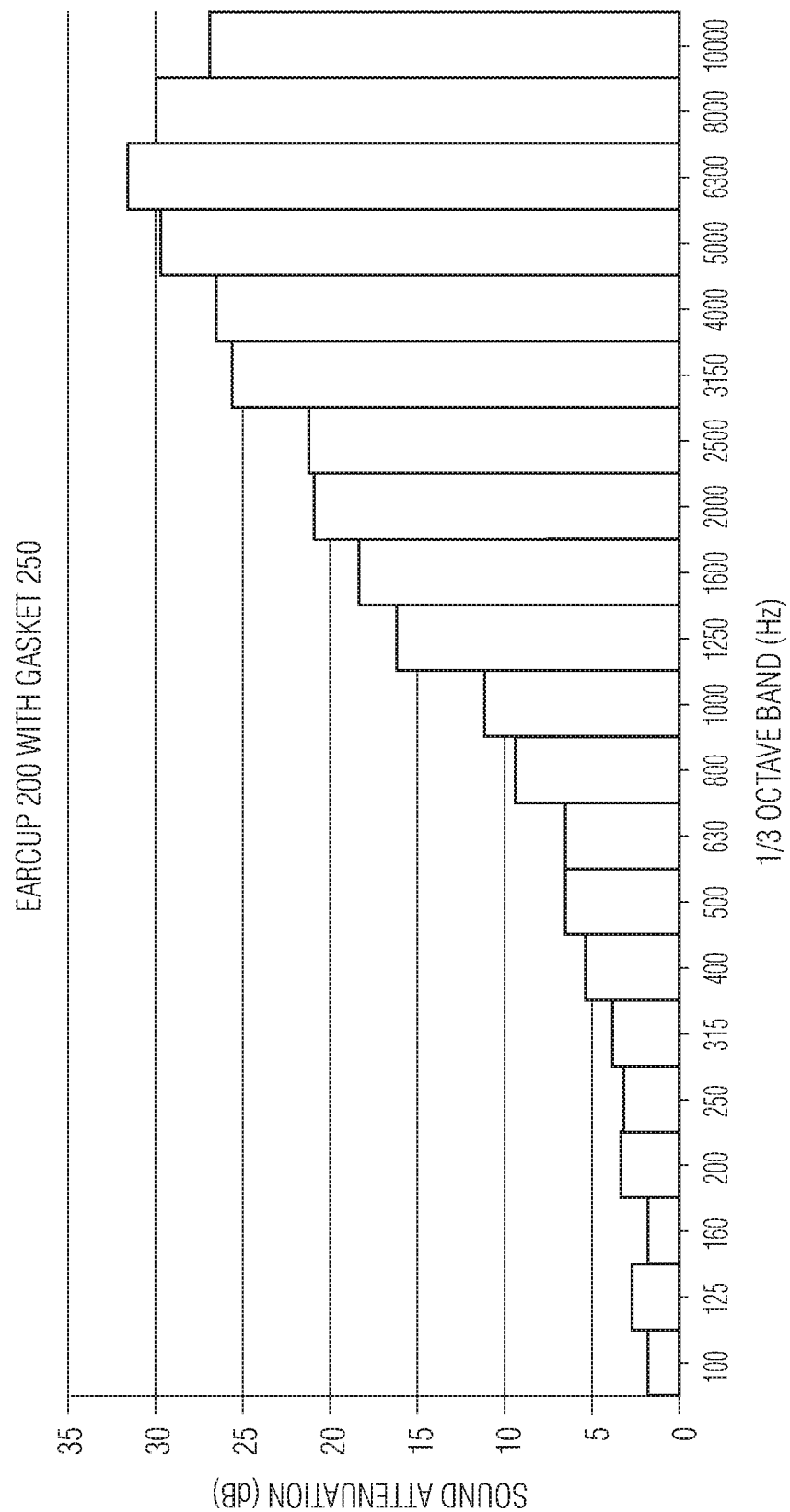
FIG. 31 is a graph of a sound attenuation of the earcup with a gasket according to an embodiment in a one-third octave band.

An exemplary graph of sound attenuation with the earcup 200 incorporating the gasket 250 of this embodiment is shown in FIG. 31. FIG. 31 is a graph of exemplary experimental results of the earcup 200 using the gasket 250; the actual attenuation provided by the earcup 200 with the gasket 250 can vary from the precise values shown in FIG. 31 according to the ranges provided below. The attenuation values shown in FIG. 31 and described below are all measured in ⅓ octave frequency bands, and conversion of the attenuation values shown in FIG. 31 and described below into one octave frequency bands can be performed according to mathematical processes known in the art.

As shown in FIG. 31, the earcup 200 with the gasket 250 according to the exemplary embodiment is a frequency-dependent auditory filter providing sound attenuation that generally increases as a function of frequency. The earcup 200 with the gasket 250 provides a sound attenuation less than or equal to 16 dB for sound frequencies of 315 Hz or less. The earcup 200 with the gasket 250 provides a sound attenuation less than 10 dB for sound frequencies of 125 Hz or less. In a range from 100 Hz to 1000 Hz, the sound attenuation generally increases as a function of frequency from less than 9 dB at 100 Hz to less than 30 dB at 1000 Hz. In an embodiment, the sound attenuation at 1000 Hz is 17-20 dB. In the shown exemplary embodiment, the sound attenuation increases from 2-3 dB at 100 Hz to 12 dB at 1000 Hz. From 2000 Hz to 10000 Hz, the sound attenuation is greater than 20 dB.

The earcup 200 with the gasket 250 provides a reduction in the overall A-weighted sound level of pink noise greater than 15 dB. The A-weighted sound level is a single value created by converting the overall sound measurements made with a source of pink noise to a single value using an A-weighted filter, as would be understood by those with ordinary skill in the art. In another embodiment, the earcup 200 with the gasket 250 provides a reduction in the overall A-weighted sound level of pink noise of 16-33 dB. In another embodiment, the earcup 200 with the gasket 250 provides a reduction in the overall A-weighted sound level of pink noise of 16-20 dB.

A gasket 250', according to another embodiment, is used with the earcup 200 in a manner structurally similar to the gasket 250 described above and shown in the embodiments of FIGS. 11, 12, and 22, but is formed of a second foam material. The second foam material of the gasket 250', in an embodiment, is an open-cell urethane foam material that has a density of approximately 20 lb/ft$^3$ and a compression force deflection value for 25% deflection of 6-14 psi. In other embodiments, the second foam material can be any open-cell foam material or any closed-cell foam material having the characteristics described herein. In other embodiments, the second foam material can be a silicone foam material.

In an embodiment, the gasket 250' is attached to the earcup 200 in only a single layer of the second foam material and has a thickness of 3 mm. In another embodiment, as with the gasket 250 shown in FIG. 22, the gasket 250' includes a first gasket layer 252 and a second gasket layer 254. Each of the first gasket layer 252 and the second gasket layer 254 has a thickness of 3 mm and the gasket 250 has a thickness of 6 mm. Each of the first gasket layer 252 and the second gasket layer 254 is formed of the second foam material in an embodiment. In another embodiment of the gasket 250', the second gasket layer 254 is formed of the second foam material and the first gasket layer 252 is formed of a third foam material. The third foam material is an open-cell urethane foam material that has a density of approximately 17 lb/ft$^3$ and a compression force deflection value for 25% deflection of 8-20 psi.

Figure 32:
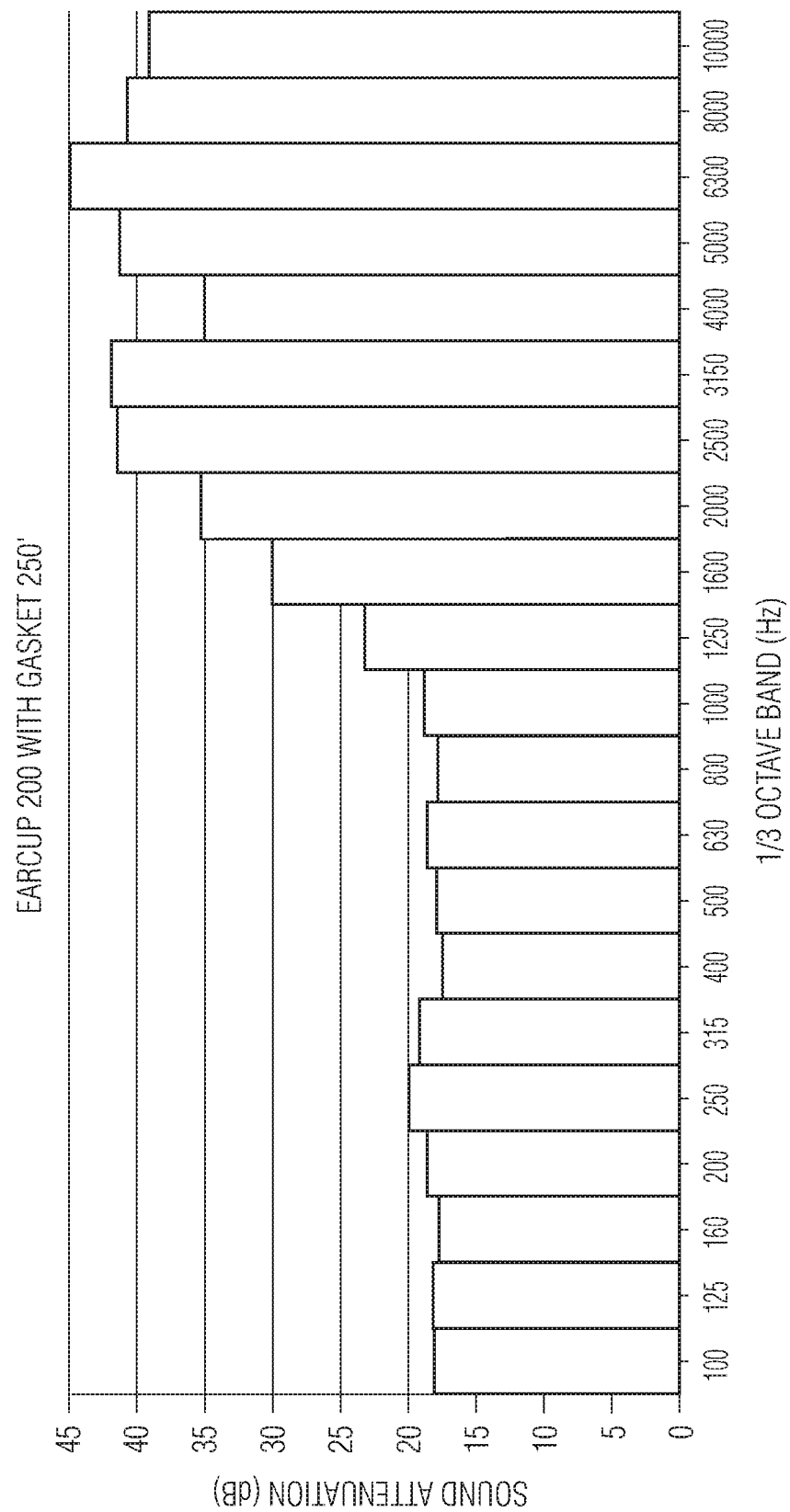
FIG. 32 is a graph of a sound attenuation of the earcup with a gasket according to another embodiment in a one-third octave band.

An exemplary graph of sound attenuation with the earcup 200 incorporating the gasket 250' of this embodiment is shown in FIG. 32. FIG. 32 is a graph of exemplary experimental results of the earcup 200 using the gasket 250'; the actual attenuation provided by the earcup 200 with the gasket 250' can vary from the precise values shown in FIG. 32 according to the ranges provided below. The attenuation values shown in FIG. 32 and described below are all measured in ⅓ octave frequency bands, and conversion of the attenuation values shown in FIG. 32 and described below into one octave frequency bands can be performed according to mathematical processes known in the art.

A graph of sound attenuation characteristics of the earcup 200 with the gasket 250' is shown in FIG. 32. The earcup 200 with the gasket 250' provides a sound attenuation greater than or equal to 10 dB for sound frequencies in a range from 80 Hz to 125 Hz. Across an entirety of a range from 100 Hz to 1000 Hz, the sound attenuation is greater than or equal to 10 dB. In an embodiment, the sound attenuation is greater than or equal to 13 dB across an entirety of a range from 100 Hz to 630 Hz. The sound attenuation remains generally constant in the range from 100 Hz to 630 Hz and, in an embodiment, is within 13-30 dB throughout an entirety of the range. In another embodiment, the sound attenuation is within 13-20 dB throughout an entirety of a range from 100 Hz to 1000 Hz. From 2000 Hz to 10000 Hz, the sound attenuation is greater than approximately 30 dB.

The earcup 200 with the gasket 250' provides a reduction in the overall A-weighted sound level of pink noise greater than 22 dB. The A-weighted sound level is a single value created by converting the overall sound measurements made with a source of pink noise to a single value using an A-weighted filter, as would be understood by those with ordinary skill in the art. In another embodiment, the earcup 200 with the gasket 250' provides a reduction in the overall A-weighted sound level of pink noise of 22-40 dB. In another embodiment, the earcup 200 with the gasket 250' provides a reduction in the overall A-weighted sound level of pink noise of 22-26 dB.

The earcup 200 with the gasket 250', like with the gasket 250, is a frequency-dependent auditory filter providing sound attenuation that generally increases as a function of frequency; the attenuation is generally higher at higher frequencies, as shown in FIG. 32. However, the earcup 200 with the gasket 250' provides a greater, more constant level of sound attenuation at lower frequencies than the earcup 200 with the gasket 250. The lower frequency range, for example below 250 Hz or around 100 Hz, is a common range for noise sounds occurring during medical transport, such as in a ground ambulance or air ambulance helicopter. In an embodiment, the earcup 200 with the gasket 250' is used in such applications to provide greater attenuation of lower frequency sound than the earcup 200 with the gasket 250.

Figure 33:
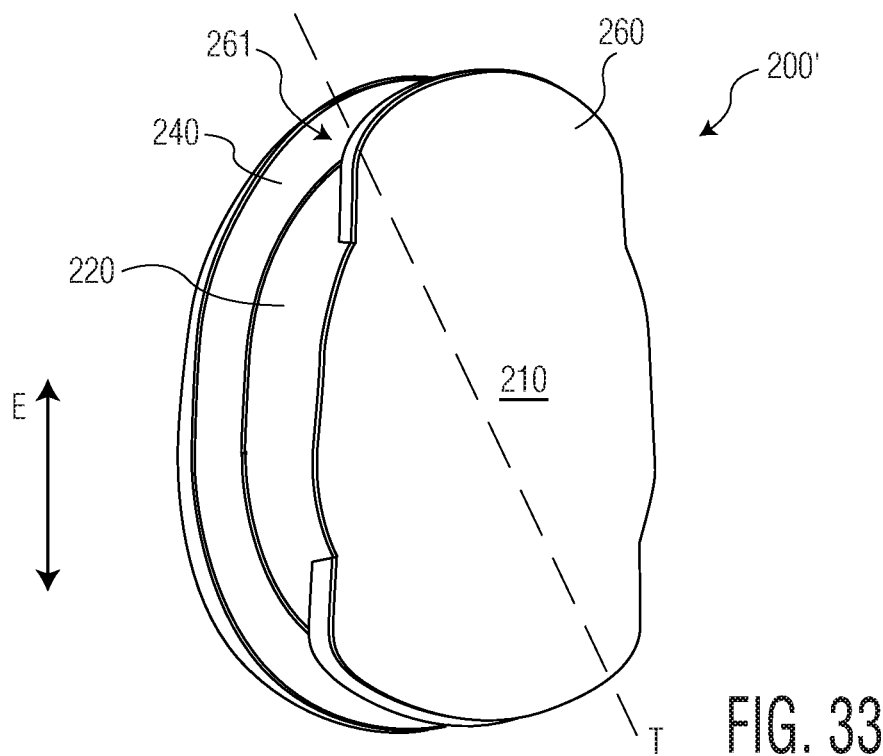
FIG. 33 is a perspective view of an earcup according to another embodiment.
Figure 34:
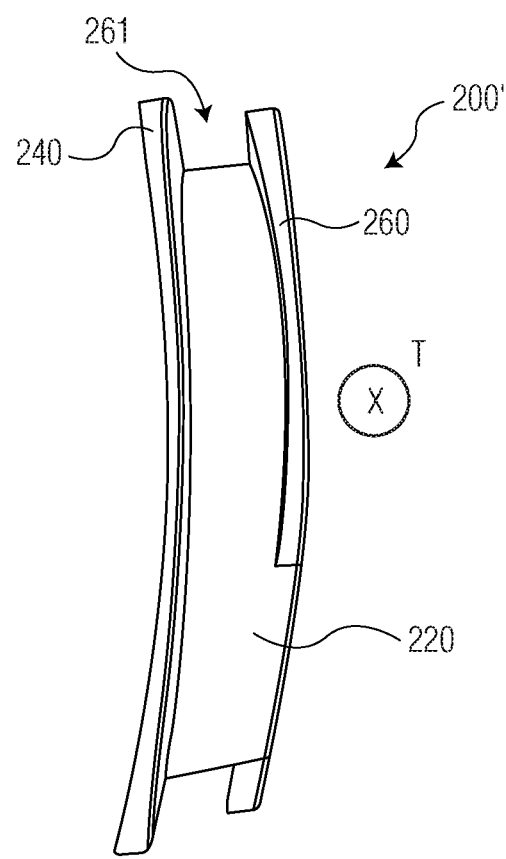
FIG. 34 is a side view of the earcup of FIG. 33.

An earcup 200' according to another embodiment is shown in FIGS. 33 and 34. Like reference numbers refer to like elements, and only the differences with respect to the earcup 200 shown in the embodiment of FIGS. 13-16 will be described in detail herein.

As shown in FIG. 33, the earcup 200' has a retaining flange 260 disposed circumferentially on the base 210 and extending radially outward from a peripheral edge of the base 210, in approximately a same plane as a surface of the base 210. The retaining flange 260 only extends from portions of the circumferential peripheral edge of the base 210. As shown in FIG. 33, the retaining flange 260 extends radially from the base 210 along a longitudinal direction E of the earcup 200'. The retaining flange 260 does not extend radially outward from the base 210 in a lateral direction perpendicular to the longitudinal direction E. In the longitudinal direction E, the retaining flange 260 protrudes beyond the sidewall 220 approximately a same distance as the flange 240 protrudes beyond the sidewall 220.

As shown in FIG. 34, in the earcup 200', both the flange 240 and the retaining flange 260 have a tapered shape. A tapering axis T, shown in FIGS. 33 and 34, extends through the earcup 200' at an acute angle with respect to the longitudinal direction E of the earcup 200'. The flange 240 and the retaining flange 260 each have a minimum thickness along the tapering axis T. The thickness of each of the flange 240 and the retaining flange 260 increases away from the tapering axis T to a maximum thickness at a point furthest from the tapering axis T.

Figure 35:
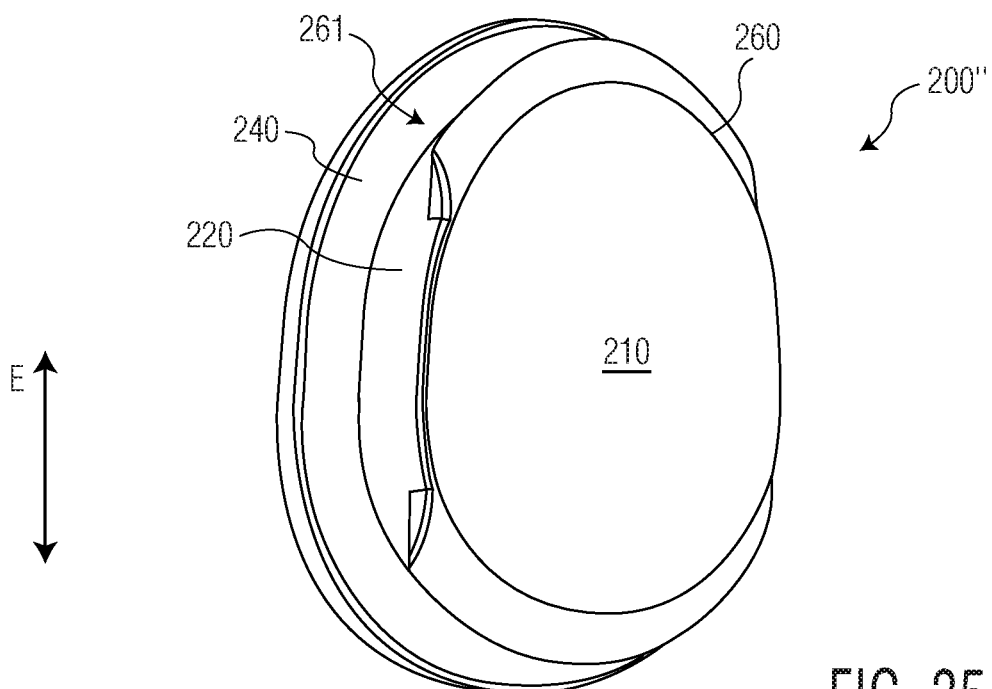
FIG. 35 is a perspective view of an earcup according to another embodiment.
Figure 36:
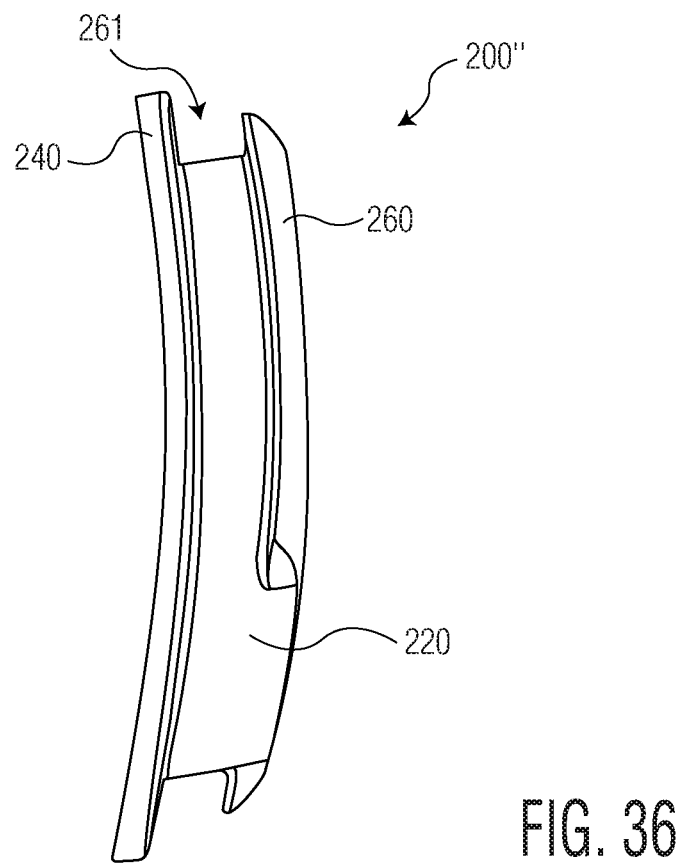
FIG. 36 is a side view of the earcup of FIG. 35.

An earcup 200" according to another embodiment is shown in FIGS. 35 and 36. Like reference numbers refer to like elements, and only the differences with respect to the earcup 200' shown in the embodiment of FIGS. 33 and 34 will be described in detail herein.

As shown in FIGS. 35 and 36, the retaining flange 260 has a rounded profile along the longitudinal direction E of the earcup 200", with the rounded profile decreasing in thickness further from the base 210 in the longitudinal direction E. In the longitudinal direction E, the retaining flange 260 protrudes beyond the sidewall 220 and may protrude a shorter distance than the flange 240 protrudes beyond the sidewall 220. The flange 240 of the earcup 200" has a constant thickness throughout an entirety of the flange 240 and the retaining flange 260 has a constant thickness at the circumferential peripheral edge of the base 210.

Figure 37:
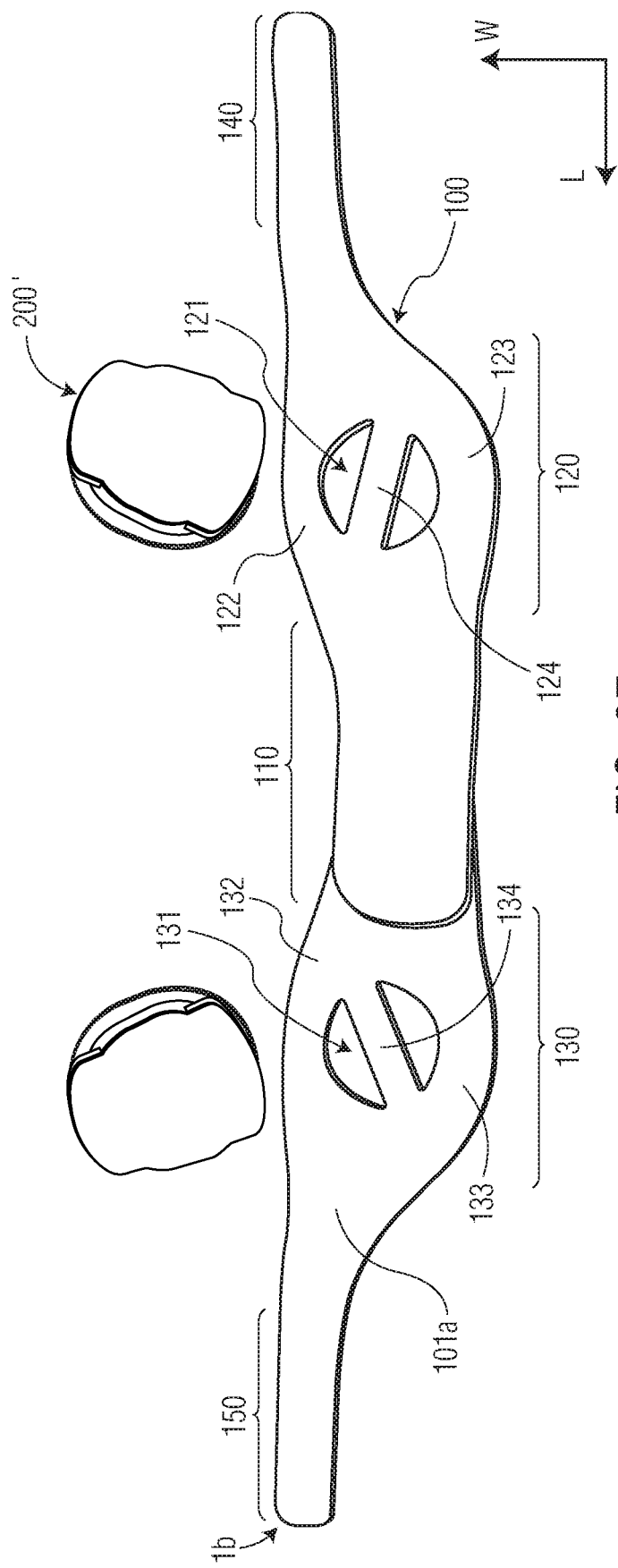
FIG. 37 is a plan view of an outer facing side of a front-closing medical headgear according to another embodiment in a state with the earcups removed.
Figure 38:
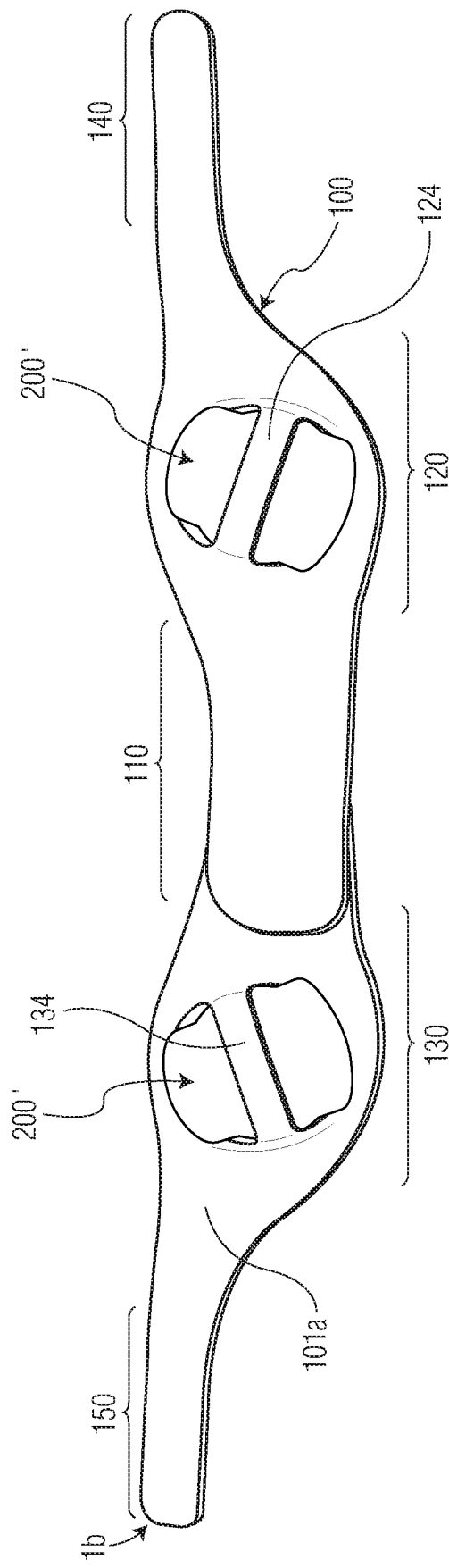
FIG. 38 is a plan view of the outer facing side of the front-closing medical headgear of FIG. 37 in a state with the earcups held in the earcup receiving spaces.

Another front closing embodiment 1b of the medical headgear 1 is shown in FIGS. 37 and 38. Like reference numbers indicate like elements and only the differences with respect to the other embodiments will be described in detail herein. In the embodiment shown in FIGS. 37 and 38, the medical headgear 1 has a first earcup strap 124 extending over the first earcup receiving space 121 and a second earcup strap 134 extending over the second earcup receiving space 131.

As shown in FIGS. 37 and 38, the earcup straps 124, 134 each are connected at a pair of opposite ends to the flexible band 100 in the elastic portions 120, 130 and extend approximately centrally over the respective earcup receiving spaces 121, 131. The earcup straps 124, 134 are positioned between the upper straps 122, 132 and the lower straps 123, 133 in the width direction W. In the shown embodiment, the earcup straps 124, 134 extend at an angle with respect to the longitudinal direction L of the medical headgear 1. In other embodiments, the earcup straps 124, 134 could extend in other directions, provided the earcup straps 124, 134 extend approximately centrally over the earcup receiving spaces 121, 131. In various embodiments, a width of each of the earcup straps 124, 134 in a plane defined by the width direction W and the longitudinal direction L is approximately equal to or less than a width of the terminating end portions 140, 150 in the same plane.

Each of the earcup straps 124, 134 is formed of a same material as the flexible band 100 and is elastically stretchable. In an embodiment, the earcup straps 124, 134 are integrally formed with the flexible band 100 by cutting out sections of the earcup receiving spaces 121, 131 that are around the earcup straps 124, 134. In another embodiment, the earcup straps 124, 134 are initially formed separately from the flexible band 100 and the opposite ends of the earcup straps 124, 134 are attached to the flexible band 100 by, for example, sewing or an adhesive. In an embodiment in which the flexible band 100 is formed form a plurality of layers, the earcup straps 124, 134 are integrally formed in or attached to an outermost layer forming the outer surface 101*a*.

As shown in FIG. 38, the earcups 200', or the earcups 200 in another embodiment, are positioned and held within the earcup receiving spaces 121, 131 as described in the embodiments above. The earcup straps 124, 134 extend over and abut the base 210 of each of the earcups 200'. The earcup straps 124, 134 are elastically stretched by the insertion of the earcups 200' and, although the earcups 200' remain held within the earcup receiving spaces 121, 131, the earcup straps 124, 134 apply an elastic force urging the earcups 200' toward the inner surface 101*b* of the flexible band 100. The earcups 200' are still removably positionable and rotatable within the earcup receiving spaces 121, 131 despite the elastic force imparted by the earcup straps 124, 134.

When a user wears the medical headgear 1 of the embodiment shown in FIGS. 37 and 38, the elastic force imparted by the earcup straps 124, 134 urges the earcups 200' toward the user's head, forming a better acoustic seal between the gasket 250 and the user's head.

While the invention has been described in detail and with reference to specific embodiments, one of ordinary skill in the art would appreciate that the described embodiments are illustrative, and that various changes and modifications can be made without departing from the scope of the invention.

What is claimed is:

1. An earcup for a medical headgear, comprising:
a body; and
a gasket attached to the body and formed of an open-cell foam, the earcup with the body and the gasket is a frequency-dependent auditory filter providing sound attenuation generally increasing as a function of frequency, the earcup with the body and the gasket provides sound attenuation of less than or equal to 16 dB throughout a frequency range less than 315 Hz.

2. The earcup of claim 1, wherein the open-cell foam is a first foam material having a compression force deflection value for 25% deflection of 0.3-3.5 psi.

3. The earcup of claim 2, wherein the first foam material has a density of approximately 15 lb/ft$^3$.

4. The earcup of claim 2, wherein the gasket includes a first gasket layer and a second gasket layer each formed of the first foam material and each having a same thickness, the first gasket layer is attached to the body and the second gasket layer is attached to the first gasket layer.

5. The earcup of claim 2, wherein the earcup with the body and the gasket provides sound attenuation increasing from less than 9 dB at a frequency of 100 Hz to a sound attenuation less than 30 dB at a frequency of 1000 Hz.

6. The earcup of claim 2, wherein the earcup with the body and the gasket provides a reduction in an overall A-weighted sound level of pink noise greater than 15 dB.

7. The earcup of claim 1, wherein the earcup with the body and the gasket provides a sound attenuation greater than 20 dB in a frequency range from 2000 Hz to 10000 Hz.

8. An earcup for a medical headgear, comprising:
a body; and
a gasket attached to the body and formed of an open-cell foam, the earcup with the body and the gasket is a frequency-dependent auditory filter providing sound attenuation generally increasing as a function of frequency, the earcup with the body and the gasket provides sound attenuation greater than 10 dB throughout a frequency range from 80 Hz to 125 Hz.

9. The earcup of claim 8, wherein the open-cell foam is a second foam material having a compression force deflection value for 25% deflection of 6-14 psi.

10. The earcup of claim 9, wherein the second foam material has a density of approximately 20 lb/ft$^3$.

11. The earcup of claim 9, wherein the gasket is formed in only a single layer attached to the body.

12. The earcup of claim 9, wherein the gasket includes a first gasket layer and a second gasket layer each having a same thickness, the first gasket layer is attached to the body and the second gasket layer is attached to the first gasket layer.

13. The earcup of claim 12, wherein the second gasket layer is formed of the second foam material and the first gasket layer is formed of a third foam material having a compression force deflection value for 25% deflection of 8-20 psi.

14. The earcup of claim 9, wherein the earcup with the body and the gasket provides a reduction in an overall A-weighted sound level of pink noise greater than 22 dB.

15. An earcup for a medical headgear, comprising:
a body; and
a gasket attached to the body and formed of an open-cell foam, the earcup with the body and the gasket is a frequency-dependent auditory filter providing sound attenuation generally increasing as a function of frequency, the open-cell foam is a first foam material having a compression force deflection value for 25% deflection of 0.3-3.5 psi, the gasket includes a first gasket layer and a second gasket layer each formed of the first foam material and each having a same thickness, the first gasket layer is attached to the body and the second gasket layer is attached to the first gasket layer.

* * * * *